US008704008B2

(12) United States Patent
Weiner et al.

(10) Patent No.: US 8,704,008 B2
(45) Date of Patent: Apr. 22, 2014

(54) PROCESS FOR PRODUCING ETHANOL USING A STACKED BED REACTOR

(75) Inventors: Heiko Weiner, Pasadena, TX (US); Zhenhua Zhou, Houston, TX (US); Radmila Jevtic, Pasadena, TX (US); Victor J. Johnston, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 122 days.

(21) Appl. No.: 13/348,590

(22) Filed: Jan. 11, 2012

(65) Prior Publication Data

US 2012/0149949 A1 Jun. 14, 2012

Related U.S. Application Data

(63) Continuation-in-part of application No. 13/094,714, filed on Apr. 26, 2011, and a continuation-in-part of application No. 13/178,659, filed on Jul. 8, 2011.

(60) Provisional application No. 61/363,056, filed on Jul. 9, 2010.

(51) Int. Cl.
$C07C\ 27/04$ (2006.01)

(52) U.S. Cl.
USPC .......................................... 568/884; 568/885

(58) Field of Classification Search
USPC ................................. 568/884, 885
See application file for complete search history.

(56) References Cited

U.S. PATENT DOCUMENTS

| | | |
|---|---|---|
| 1,939,116 A | 12/1933 | Fuchs |
| 2,607,807 A | 8/1952 | Ford |
| 2,649,407 A | 8/1953 | Harrison et al. |
| 2,702,783 A | 2/1955 | Harrison et al. |
| 2,801,209 A | 7/1957 | Muller et al. |
| 2,882,244 A | 4/1959 | Milton |
| 3,102,150 A | 8/1963 | Hunter et al. |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Karl et al. |
| 3,709,795 A | 1/1973 | Singleton |
| 3,769,329 A | 10/1973 | Knox et al. |
| 3,864,284 A | 2/1975 | Clippinger et al. |
| 3,884,981 A | 5/1975 | Kiff |
| 3,925,490 A | 12/1975 | Reich et al. |
| 3,990,952 A | 11/1976 | Katzen |
| 4,008,131 A | 2/1977 | Price |
| 4,039,395 A | 8/1977 | Eby |
| 4,107,002 A | 8/1978 | Eck et al. |
| 4,126,539 A | 11/1978 | Derr, Jr. et al. |
| 4,149,940 A | 4/1979 | Pinto |
| 4,262,154 A | 4/1981 | Gane et al. |
| 4,275,228 A | 6/1981 | Gruffaz et al. |
| 4,306,942 A | 12/1981 | Brush et al. |
| 4,317,918 A | 3/1982 | Takano et al. |
| 4,319,058 A | 3/1982 | Kulpranthipanja et al. |
| 4,328,375 A | 5/1982 | Barlow |
| 4,338,221 A | 7/1982 | Qualeatti |
| 4,352,940 A | 10/1982 | Adelman et al. |
| 4,352,947 A | 10/1982 | Habib et al. |
| 4,370,491 A | 1/1983 | Bott et al. |
| 4,379,028 A | 4/1983 | Berg et al. |
| 4,395,576 A | 7/1983 | Kwantes et al. |
| 4,398,039 A | 8/1983 | Pesa et al. |
| 4,409,405 A | 10/1983 | Lin et al. |
| 4,421,939 A | 12/1983 | Kiff et al. |
| 4,422,903 A | 12/1983 | Messick et al. |
| 4,429,056 A | 1/1984 | Smith |
| 4,430,506 A | 2/1984 | Gauthier-Lafaye et al. |
| 4,443,639 A | 4/1984 | Pesa et al. |
| 4,451,677 A | 5/1984 | Bradley et al. |
| 4,454,358 A | 6/1984 | Kummer et al. |
| 4,456,775 A | 6/1984 | Travers et al. |
| 4,465,854 A | 8/1984 | Pond et al. |
| 4,471,136 A | 9/1984 | Larkins et al. |
| 4,476,326 A | 10/1984 | Lin et al. |
| 4,480,115 A | 10/1984 | McGinnis |
| 4,481,146 A | 11/1984 | Leupold et al. |
| 4,492,808 A | 1/1985 | Hagen et al. |
| 4,497,967 A | 2/1985 | Wan |
| 4,514,515 A | 4/1985 | Travers et al. |
| 4,514,521 A | 4/1985 | Smith |
| 4,517,391 A | 5/1985 | Schuster et al. |
| 4,520,213 A | 5/1985 | Victor |
| 4,541,897 A | 9/1985 | Sommer et al. |
| 4,556,644 A | 12/1985 | Erpenbach et al. |
| 4,569,726 A | 2/1986 | Berg et al. |
| 4,611,085 A | 9/1986 | Kitson |

(Continued)

FOREIGN PATENT DOCUMENTS

| | | |
|---|---|---|
| CA | 1233484 | 3/1988 |
| CN | 1230458 | 10/1999 |

(Continued)

OTHER PUBLICATIONS

International Search Report and Written Opinion mailed Sep. 2, 2011 in corresponding International Application No. PCT/US2011/023276.
Written Opinion mailed May 8, 2012 in corresponding International Application No. PCT/US2011/023276.
International Preliminary Report on Patentability mailed Jun. 27, 2012 in corresponding International Application No. PCT/US2011/023276.
International Search Report and Written Opinion mailed on Aug. 11, 2011 in corresponding International Application No. PCT/US2011/023283.
Written Opinion mailed on Jan. 30, 2012 in corresponding International Application No. PCT/US2011/023283.
Invitation to Pay Additional Fees and Partial Search Report mailed May 4, 2011 in corresponding International Application No. PCT/US2011/023283.
International Preliminary Report on Patentability mailed May 18, 2012 in corresponding International Application No. PCT/US2011/023283.

(Continued)

Primary Examiner — Sikarl Witherspoon

(57) ABSTRACT

The present invention produces ethanol in a stacked bed reactor that comprises a first catalyst comprising platinum and tin and a second catalyst comprising copper or an oxide thereof. The crude ethanol product may be separated and ethanol recovered.

34 Claims, 5 Drawing Sheets

(56) References Cited

U.S. PATENT DOCUMENTS

| | | |
|---|---|---|
| 4,626,321 A | 12/1986 | Grethlein et al. |
| 4,626,604 A | 12/1986 | Hiles et al. |
| 4,628,130 A | 12/1986 | Bournonville et al. |
| 4,629,711 A | 12/1986 | Erpenbach et al. |
| 4,664,753 A | 5/1987 | Erpenbach et al. |
| 4,678,543 A | 7/1987 | Houben et al. |
| 4,692,218 A | 9/1987 | Houben et al. |
| 4,737,318 A | 4/1988 | Ichino et al. |
| 4,751,334 A | 6/1988 | Turner et al. |
| 4,758,600 A | 7/1988 | Arimitsu et al. |
| 4,762,817 A | 8/1988 | Logsdon et al. |
| 4,777,303 A | 10/1988 | Kitson et al. |
| 4,804,791 A | 2/1989 | Kitson et al. |
| 4,826,795 A | 5/1989 | Kitson et al. |
| 4,837,367 A | 6/1989 | Gustafson et al. |
| 4,837,368 A | 6/1989 | Gustafson et al. |
| 4,842,693 A | 6/1989 | Wheldon |
| 4,886,905 A | 12/1989 | Larkins et al. |
| 4,908,477 A | 3/1990 | Hartmann et al. |
| 4,961,826 A | 10/1990 | Grethlein et al. |
| 4,978,778 A | 12/1990 | Isshiki et al. |
| 4,985,572 A | 1/1991 | Kitson et al. |
| 4,990,655 A | 2/1991 | Kitson et al. |
| 4,992,582 A | 2/1991 | Ruppert et al. |
| 4,994,608 A | 2/1991 | Torrence et al. |
| 5,001,259 A | 3/1991 | Smith et al. |
| 5,004,845 A | 4/1991 | Bradley et al. |
| 5,026,908 A | 6/1991 | Smith et al. |
| 5,035,776 A | 7/1991 | Knapp |
| 5,047,592 A | 9/1991 | Carpenter |
| 5,061,671 A | 10/1991 | Kitson et al. |
| 5,070,016 A | 12/1991 | Hallberg |
| 5,124,004 A | 6/1992 | Grethlein et al. |
| 5,144,068 A | 9/1992 | Smith et al. |
| 5,149,680 A | 9/1992 | Kitson et al. |
| 5,185,476 A | 2/1993 | Gustafson |
| 5,185,481 A | 2/1993 | Muto et al. |
| 5,196,601 A | 3/1993 | Kitsuki et al. |
| 5,198,592 A | 3/1993 | Van Beijnum et al. |
| 5,215,902 A | 6/1993 | Tedder |
| 5,220,020 A | 6/1993 | Buchwald et al. |
| 5,227,141 A | 7/1993 | Kim et al. |
| 5,233,099 A | 8/1993 | Tabata et al. |
| 5,237,108 A | 8/1993 | Marraccini et al. |
| 5,241,106 A | 8/1993 | Inoue et al. |
| 5,243,095 A | 9/1993 | Roberts et al. |
| 5,250,271 A | 10/1993 | Horizoe et al. |
| 5,254,758 A | 10/1993 | Hiles et al. |
| 5,300,685 A | 4/1994 | Scates et al. |
| 5,334,751 A | 8/1994 | Lemanski et al. |
| 5,348,625 A | 9/1994 | Berg |
| 5,362,918 A | 11/1994 | Aizawa et al. |
| 5,399,752 A | 3/1995 | Okrasinski et al. |
| 5,403,962 A | 4/1995 | Schneider et al. |
| 5,414,161 A | 5/1995 | Uhm et al. |
| 5,415,741 A | 5/1995 | Berg |
| 5,416,237 A | 5/1995 | Aubigne et al. |
| 5,426,246 A | 6/1995 | Nagahara et al. |
| 5,437,770 A | 8/1995 | Berg |
| 5,445,716 A | 8/1995 | Berg |
| 5,449,440 A | 9/1995 | Rescalli et al. |
| 5,476,974 A | 12/1995 | Moore et al. |
| 5,480,665 A | 1/1996 | Smith |
| 5,502,094 A | 3/1996 | Moore et al. |
| 5,502,248 A | 3/1996 | Funk et al. |
| 5,527,969 A | 6/1996 | Kaufhold et al. |
| 5,567,765 A | 10/1996 | Moore et al. |
| RE35,377 E | 11/1996 | Steinberg et al. |
| 5,599,976 A | 2/1997 | Scates et al. |
| 5,658,962 A | 8/1997 | Moore et al. |
| 5,696,284 A | 12/1997 | Baker et al. |
| 5,731,252 A | 3/1998 | Warner et al. |
| 5,747,486 A | 5/1998 | Sohda et al. |
| 5,762,765 A | 6/1998 | Berg |
| 5,770,761 A | 6/1998 | Lin et al. |
| 5,770,770 A | 6/1998 | Kim et al. |
| 5,800,681 A | 9/1998 | Berg |
| 5,821,111 A | 10/1998 | Gaddy et al. |
| 5,831,133 A | 11/1998 | Mimoun |
| 5,861,530 A | 1/1999 | Atkins et al. |
| 5,877,347 A | 3/1999 | Ditzel et al. |
| 5,877,348 A | 3/1999 | Ditzel et al. |
| 5,883,295 A | 3/1999 | Sunley et al. |
| 5,932,764 A | 8/1999 | Morris et al. |
| 5,942,460 A | 8/1999 | Garland et al. |
| 5,973,193 A | 10/1999 | Crane et al. |
| 5,993,610 A | 11/1999 | Berg |
| 5,998,658 A | 12/1999 | Wu et al. |
| 6,024,176 A | 2/2000 | Moore et al. |
| 6,040,474 A | 3/2000 | Jobson et al. |
| 6,046,127 A | 4/2000 | Mimoun |
| 6,093,845 A | 7/2000 | Van Acker et al. |
| 6,121,497 A | 9/2000 | Murphy |
| 6,121,498 A | 9/2000 | Tustin et al. |
| 6,140,535 A | 10/2000 | Williams |
| 6,143,930 A | 11/2000 | Singh et al. |
| 6,204,299 B1 | 3/2001 | Moore et al. |
| 6,214,253 B1 | 4/2001 | Moore et al. |
| 6,232,352 B1 | 5/2001 | Vidalin et al. |
| 6,294,703 B1 | 9/2001 | Hara et al. |
| 6,326,515 B1 | 12/2001 | Clode et al. |
| 6,361,713 B1 | 3/2002 | Moore et al. |
| 6,375,807 B1 | 4/2002 | Nieuwoudt et al. |
| 6,403,840 B1 | 6/2002 | Zhou et al. |
| 6,458,996 B1 | 10/2002 | Muskett |
| 6,462,231 B1 | 10/2002 | Yanagawa et al. |
| 6,462,243 B1 | 10/2002 | Zhou et al. |
| 6,465,696 B1 | 10/2002 | Zhou et al. |
| 6,465,699 B1 | 10/2002 | Grosso |
| 6,472,555 B2 | 10/2002 | Choudary et al. |
| 6,472,572 B1 | 10/2002 | Zhou et al. |
| 6,486,366 B1 | 11/2002 | Ostgard et al. |
| 6,486,368 B1 | 11/2002 | Zhou et al. |
| 6,491,983 B2 | 12/2002 | Moore et al. |
| 6,495,730 B1 | 12/2002 | Konishi et al. |
| 6,509,180 B1 | 1/2003 | Verser et al. |
| 6,509,290 B1 | 1/2003 | Vaughn et al. |
| 6,525,230 B2 | 2/2003 | Grosso |
| 6,552,220 B1 | 4/2003 | Obana et al. |
| 6,627,770 B1 | 9/2003 | Cheung et al. |
| 6,632,330 B1 | 10/2003 | Colley et al. |
| 6,657,078 B2 | 12/2003 | Scates et al. |
| 6,670,490 B1 | 12/2003 | Campos et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,713,655 B2 | 3/2004 | Yilmaz et al. |
| 6,723,886 B2 | 4/2004 | Allison et al. |
| 6,755,975 B2 | 6/2004 | Vane et al. |
| 6,765,110 B2 | 7/2004 | Warner et al. |
| 6,768,021 B2 | 7/2004 | Horan et al. |
| 6,809,217 B1 | 10/2004 | Colley et al. |
| 6,863,211 B2 | 3/2005 | Moore et al. |
| 6,867,164 B2 | 3/2005 | Obana et al. |
| 6,903,045 B2 | 6/2005 | Zoeller et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,019,182 B2 | 3/2006 | Grosso |
| 7,074,603 B2 | 7/2006 | Verser et al. |
| 7,084,312 B1 | 8/2006 | Huber et al. |
| 7,091,155 B2 | 8/2006 | Inui et al. |
| 7,115,772 B2 | 10/2006 | Picard et al. |
| 7,148,390 B2 | 12/2006 | Zhou et al. |
| 7,161,050 B2 | 1/2007 | Sherman et al. |
| 7,208,624 B2 | 4/2007 | Scates et al. |
| 7,223,886 B2 | 5/2007 | Scates et al. |
| 7,230,150 B2 | 6/2007 | Grosso et al. |
| 7,297,236 B1 | 11/2007 | Vander et al. |
| 7,351,559 B2 | 4/2008 | Verser et al. |
| 7,361,794 B2 | 4/2008 | Grosso |
| 7,375,049 B2 | 5/2008 | Hayes et al. |
| 7,399,892 B2 | 7/2008 | Rix et al. |
| 7,507,562 B2 | 3/2009 | Verser et al. |

(56) References Cited

U.S. PATENT DOCUMENTS

| | | |
|---|---|---|
| 7,538,060 B2 | 5/2009 | Barnicki et al. |
| 7,553,397 B1 | 6/2009 | Colley et al. |
| 7,572,353 B1 | 8/2009 | Vander et al. |
| 7,601,865 B2 | 10/2009 | Verser et al. |
| 7,608,744 B1 | 10/2009 | Johnston et al. |
| 7,652,167 B2 | 1/2010 | Miller et al. |
| 7,667,068 B2 | 2/2010 | Miller et al. |
| 7,678,940 B2 | 3/2010 | Miura et al. |
| 7,682,812 B2 | 3/2010 | Verser et al. |
| 7,700,814 B2 | 4/2010 | Garton et al. |
| 7,732,173 B2 | 6/2010 | Mairal et al. |
| 7,744,727 B2 | 6/2010 | Blum et al. |
| 7,820,852 B2 | 10/2010 | Johnston et al. |
| 7,834,223 B2 | 11/2010 | Atkins et al. |
| 7,838,708 B2 | 11/2010 | Sherman et al. |
| 7,842,844 B2 | 11/2010 | Atkins et al. |
| 7,863,489 B2 | 1/2011 | Johnston et al. |
| 7,884,253 B2 | 2/2011 | Stites et al. |
| 7,888,082 B2 | 2/2011 | Verser et al. |
| 7,906,680 B2 | 3/2011 | Scates et al. |
| 7,947,746 B2 | 5/2011 | Daniel et al. |
| 7,964,379 B2 | 6/2011 | Verser et al. |
| 7,994,368 B2 | 8/2011 | Johnston et al. |
| 8,071,821 B2 | 12/2011 | Johnston et al. |
| 2001/0027172 A1 | 10/2001 | Moore et al. |
| 2002/0156328 A1 | 10/2002 | Grosso |
| 2002/0198416 A1 | 12/2002 | Zhou et al. |
| 2003/0013908 A1 | 1/2003 | Horan et al. |
| 2003/0069452 A1 | 4/2003 | Sherman et al. |
| 2003/0077771 A1 | 4/2003 | Verser et al. |
| 2003/0078456 A1 | 4/2003 | Yilmaz et al. |
| 2003/0104587 A1 | 6/2003 | Verser et al. |
| 2003/0114719 A1 | 6/2003 | Fischer et al. |
| 2003/0120121 A1 | 6/2003 | Sherman et al. |
| 2003/0125585 A1 | 7/2003 | Yilmaz et al. |
| 2003/0125589 A1 | 7/2003 | Grosso |
| 2003/0135069 A1 | 7/2003 | Fujita et al. |
| 2003/0153059 A1 | 8/2003 | Pilkington et al. |
| 2003/0166973 A1 | 9/2003 | Zhou et al. |
| 2004/0006246 A1 | 1/2004 | Sherman et al. |
| 2004/0009614 A1 | 1/2004 | Ahn et al. |
| 2004/0063184 A1 | 4/2004 | Grichko |
| 2004/0152915 A1 | 8/2004 | Fujita et al. |
| 2004/0232049 A1 | 11/2004 | Dath et al. |
| 2004/0242917 A1 | 12/2004 | Inui et al. |
| 2004/0267074 A1 | 12/2004 | Grosso et al. |
| 2005/0043572 A1 | 2/2005 | Grosso |
| 2005/0192468 A1 | 9/2005 | Sherman et al. |
| 2005/0209328 A1 | 9/2005 | Allgood et al. |
| 2005/0214408 A1 | 9/2005 | Pilkington et al. |
| 2006/0019360 A1 | 1/2006 | Verser et al. |
| 2006/0106246 A1 | 5/2006 | Modesitt |
| 2006/0127999 A1 | 6/2006 | Verser et al. |
| 2006/0224013 A1 | 10/2006 | Inui et al. |
| 2006/0247466 A1 | 11/2006 | Zinobile et al. |
| 2006/0252956 A1 | 11/2006 | Miller et al. |
| 2007/0031954 A1 | 2/2007 | Mairal et al. |
| 2007/0265360 A1 | 11/2007 | Luo et al. |
| 2007/0270511 A1 | 11/2007 | Melnichuk et al. |
| 2008/0103335 A1 | 5/2008 | Scates et al. |
| 2008/0135396 A1 | 6/2008 | Blum |
| 2008/0187472 A1 | 8/2008 | Ahn et al. |
| 2008/0193989 A1 | 8/2008 | Verser et al. |
| 2008/0207953 A1 | 8/2008 | Houssin et al. |
| 2008/0257784 A1 | 10/2008 | Dath et al. |
| 2008/0269518 A1 | 10/2008 | Scates et al. |
| 2009/0005588 A1 | 1/2009 | Hassan et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0099389 A1 | 4/2009 | Shaver |
| 2009/0166172 A1 | 7/2009 | Casey et al. |
| 2009/0221725 A1 | 9/2009 | Chornet et al. |
| 2009/0264285 A1 | 10/2009 | Luo et al. |
| 2009/0270651 A1 | 10/2009 | Zinobile et al. |
| 2009/0281354 A1 | 11/2009 | Mariansky et al. |
| 2009/0299092 A1 | 12/2009 | Beavis et al. |
| 2009/0318573 A1 | 12/2009 | Stites et al. |
| 2009/0326080 A1 | 12/2009 | Chornet et al. |
| 2009/0326268 A1 | 12/2009 | Hanes et al. |
| 2010/0016454 A1 | 1/2010 | Gracey et al. |
| 2010/0029980 A1 | 2/2010 | Johnston et al. |
| 2010/0029993 A1 | 2/2010 | Johnston et al. |
| 2010/0029995 A1 | 2/2010 | Johnston et al. |
| 2010/0029996 A1 | 2/2010 | Danjo et al. |
| 2010/0030001 A1 | 2/2010 | Chen et al. |
| 2010/0030002 A1 | 2/2010 | Johnston et al. |
| 2010/0041919 A1 | 2/2010 | Wu et al. |
| 2010/0063319 A1 | 3/2010 | Brtko et al. |
| 2010/0069515 A1 | 3/2010 | Tirtowidjojo et al. |
| 2010/0080736 A1 | 4/2010 | Hassan et al. |
| 2010/0121114 A1 | 5/2010 | Johnston et al. |
| 2010/0121119 A1 | 5/2010 | Sherman et al. |
| 2010/0137630 A1 | 6/2010 | Garton et al. |
| 2010/0145097 A1 | 6/2010 | Brtko et al. |
| 2010/0185021 A1 | 7/2010 | Ross et al. |
| 2010/0196789 A1 | 8/2010 | Fisher et al. |
| 2010/0197485 A1 | 8/2010 | Johnston et al. |
| 2010/0197959 A1 | 8/2010 | Johnston et al. |
| 2010/0197985 A1 | 8/2010 | Johnston et al. |
| 2010/0204512 A1 | 8/2010 | Kimmich et al. |
| 2010/0249479 A1 | 9/2010 | Berg-Slot et al. |
| 2010/0261800 A1 | 10/2010 | Daniel et al. |
| 2010/0273229 A1 | 10/2010 | Verser et al. |
| 2010/0311138 A1 | 12/2010 | Padgett |
| 2011/0004033 A1 | 1/2011 | Johnston et al. |
| 2011/0004034 A1 | 1/2011 | Daniel et al. |
| 2011/0034741 A1 | 2/2011 | Sherman et al. |
| 2011/0046421 A1 | 2/2011 | Daniel et al. |
| 2011/0082322 A1 | 4/2011 | Jevtic et al. |
| 2011/0098501 A1 | 4/2011 | Johnston et al. |
| 2011/0190547 A1 | 8/2011 | Jevtic et al. |
| 2011/0190548 A1 | 8/2011 | Jevtic et al. |
| 2011/0190552 A1 | 8/2011 | Powell et al. |
| 2011/0224462 A1 | 9/2011 | Ditzel et al. |
| 2011/0263911 A1 | 10/2011 | Johnston et al. |
| 2011/0275861 A1 | 11/2011 | Johnston et al. |
| 2011/0275862 A1 | 11/2011 | Johnston et al. |
| 2012/0010438 A1 | 1/2012 | Lee et al. |
| 2012/0010445 A1 | 1/2012 | Johnston et al. |
| 2012/0149949 A1 | 6/2012 | Weiner et al. |

FOREIGN PATENT DOCUMENTS

| | | |
|---|---|---|
| CN | 1944373 | 4/2007 |
| CN | 1944374 | 4/2007 |
| CN | 101665424 | 3/2010 |
| CN | 201768393 | 3/2011 |
| CN | 102228831 | 11/2011 |
| CN | 102229520 | 11/2011 |
| DD | 241590 | 12/1986 |
| DE | 60025239 | 6/2006 |
| EP | 0056488 | 7/1982 |
| EP | 0104197 | 4/1984 |
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0285420 | 10/1988 |
| EP | 0285786 | 10/1988 |
| EP | 0400904 | 5/1990 |
| EP | 0372847 | 6/1990 |
| EP | 0456647 | 11/1991 |
| EP | 0553825 | 5/1996 |
| EP | 0944572 | 9/1999 |
| EP | 0990638 | 4/2000 |
| EP | 0992482 | 4/2000 |
| EP | 1338587 | 8/2003 |
| EP | 2060553 | 5/2009 |
| EP | 2060555 | 5/2009 |
| EP | 2072487 | 6/2009 |
| EP | 2072488 | 6/2009 |

(56) References Cited

FOREIGN PATENT DOCUMENTS

| | | |
|---|---|---|
| EP | 2072489 | 6/2009 |
| EP | 2072492 | 6/2009 |
| EP | 2186787 | 5/2010 |
| JP | 60-09454 | 1/1985 |
| JP | 60-25033 | 2/1985 |
| JP | 61-28181 | 2/1986 |
| JP | 2-215790 | 8/1990 |
| JP | 4-193304 | 7/1992 |
| JP | 5-186391 | 7/1993 |
| JP | 6-116182 | 4/1994 |
| JP | 2001-046874 | 2/2001 |
| JP | 2001-157841 | 6/2001 |
| JP | 2005-289936 | 10/2005 |
| KR | 2012 0010763 | 2/2012 |
| WO | WO 82/03854 | 11/1982 |
| WO | WO 83/03409 | 10/1983 |
| WO | WO 98/25876 | 6/1998 |
| WO | WO 02/092541 | 11/2002 |
| WO | WO 2005/102513 | 11/2005 |
| WO | WO 2007/003897 | 1/2007 |
| WO | WO 2008/135192 | 11/2008 |
| WO | WO 2009/009320 | 1/2009 |
| WO | WO 2009/009322 | 1/2009 |
| WO | WO 2009/009323 | 1/2009 |
| WO | WO 2009/048335 | 4/2009 |
| WO | WO 2009/063174 | 5/2009 |
| WO | WO 2009/063176 | 5/2009 |
| WO | WO 2009/077719 | 6/2009 |
| WO | WO 2009/077720 | 6/2009 |
| WO | WO 2009/077725 | 6/2009 |
| WO | WO 2009/077729 | 6/2009 |
| WO | WO 2009/103948 | 8/2009 |
| WO | WO 2009/105860 | 9/2009 |
| WO | WO 2010/014145 | 2/2010 |
| WO | WO 2010/014151 | 2/2010 |
| WO | WO 2010/014153 | 2/2010 |
| WO | WO 2010/030320 | 3/2010 |
| WO | WO 2010/055285 | 5/2010 |
| WO | WO 2011/053365 | 5/2011 |
| WO | WO 2011/056597 | 5/2011 |
| WO | WO 2011/097193 | 8/2011 |
| WO | WO 2011/097208 | 8/2011 |
| WO | WO 2011/097219 | 8/2011 |
| WO | WO 2012/006228 | 1/2012 |
| WO | WO 2012/006499 | 1/2012 |

OTHER PUBLICATIONS

International Search Report and Written Opinion mailed Sep. 6, 2011 in corresponding International Application No. PCT/US2011/023338.

Written Opinion mailed May 16, 2012 in corresponding International Application No. PCT/US2011/023338.

International Preliminary Report on Patentability mailed Jul. 5, 2012 in corresponding International Application No. PCT/US2011/023338.

International Search Report and Written Opinion mailed May 31, 2012 in corresponding International Application No. PCT/US2011/043213.

Witzeman and Agreda in "Acetic Acid and its Derivatives,", Marcel Dekker, NY, 1992, p. 271.

US Office Action mailed May 3, 2012 in corresponding U.S. Appl. No. 12/833,737.

International Search Report and Written Opinion mailed Jun. 11, 2012 in corresponding International Application No. PCT/US2012/020977.

International Search Report and Written Opinion mailed Mar. 14, 2012 in corresponding International Application No. PCT/US2012/020979.

Pestman et al., Identification of the Active Sites in the Selective Hydrogenation of Acetic Acid to Acetaldehyde on Iron Oxide Catalysts, Journal of Catalysis 174:142-152 (1998).

International Search Report and Written Opinion for PCT/US2011/043310 dated Feb. 23, 2012.

Spivey et al., "Heterogeneous catalytic synthesis of ethanol from biomass-dervied syngas," Chemical Society Review, 2007, vol. 36, pp. 1514-1528.

Michael Gauβ, et al., Applied Homogeneous Catalysis with Organometallic Compounds: A Comprehensive Handbook in two Volume, Chapter 2.1, p. 27-200, (1st ed., 1996).

International Search Report and Written Opinion mailed Jul. 12, 2012 in corresponding International Application No. PCT/US2012/035166.

Rachmady, Acetic Acid Reduction by H2 on Bimetallic Pt-Fe Catalysts, Journal of Catalysis 209, 87-98, Apr. 1, 2002, Elsevier Science (USA).

J. Jones, et al., "The Cativa™ Process for the Manufacture of Acetic Acid", Platinum Metals Review, vol. 44, No. 3, pp. 94-104 (Jul. 2000).

Hilmen, Separation of Azeotropic Mixtures: Tools for Analysis and Studies on Batch Distillation Operation (Nov. 2000) pp. 17-20.

International Search Report and Written Opinion mailed Jul. 6, 2012 in corresponding International Application No. PCT/US2011/059889.

Marian Simo et al., "Adsorption/Desorption of Water and Ethanol on 3A Zeolite in Near-Adiabatic Fixed Bed", Ind. Eng. Chem. Res., 2009, 48, 9247-9260.

N. Calvar et al., "Esterification of acetic acid with ethanol: Reaction kinetics and operation in a packed bed reactive distillation column", Chemical Engineering and Processing, 46 (207) 1317—1323.

Hidetoshi Kita et al., "Synthesis of a zeolite NaA membrane for pervaporation of water/organic liquid mixtures", Journal of Materials Science Letters, 14 (1995) 206—208.

International Search Report and Written Opinion mailed Jul. 30, 2012 in corresponding International Application No. PCT/US2012/035273.

Tracy J. Benson et al., "Cellulose Based Adsorbent Materials for the Dehydration of Ethanol Using Thermal Swing Adsorption", Adsorption, Kluwer Academic Publishers, vol. 11, No. 1, Jul. 1, 2005, pp. 697-701, XP 019203738.

Yu Huang et al., "Low-Energy Distillation-Membrane separation Process" Industrial & Engineering Chemistry Research, American Chemical Society, US, vol. 49, No. 8, Jan. 1, 2010, pp. 3760-3768, XP 002657719.

International Search Report and Written Opinion mailed Jul. 11, 2012 in corresponding International Application No. PCT/US2012/035203.

International Search Report and Written Opinion mailed Aug. 2, 2012 in corresponding International Application No. PCT/US2012/035220.

International Search Report and Written Opinion mailed Jul. 30, 2012 in corresponding International Application No. PCT/US2012/035189.

International Search Report and Written Opinion mailed Jul. 12, 2012 in corresponding International Application No. PCT/US2012/035178.

Subramani et al., "A Review of Recent Literature to Search for an Efficient Catalytic Process for the Conversion of Syngas to Ethanol," Energy & Fuels, 2008, vol. 22, pp. 814-839.

Juran et al., "Convert Methanol to Ethanol", Hydrocarbon Processing, Oct. 1985, pp. 85-87.

Zhang et al., "Hydrogenation of Ethyl Acetate to Ethanol over Ni-Based Catalysts Obtained from Ni/Al Hydrotalcite-Like Compounds", Molecules 2010, 15, 5139-5152, 2010.

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

Santori et al.(2000). Hydrogenation of carbonylic compounds on Pt/SiO2 catalysts modified with SnBu4, Studies in Surface Science and Catalysis, 130, 2063-2068.

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

(56) References Cited

OTHER PUBLICATIONS

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Claus, et al., "Selective Hydrogenolysis of Methyl and Ethyl Acetate in the Gas Phase on Copper and Supported Group VIII Metal Catalysts", Applied Catalysis A, 79, 1991, pp. 1-18.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

Invitation to Pay Fees for PCT/US2012/020977 dated Mar. 13, 2012.

International Preliminary Report on Patentability for PCT/US2011/043310 mailed Oct. 22, 2012.

International Preliminary Report on Patentability for PCT/US2011/042639 mailed Nov. 9, 2012.

International Search Report and Written Opinion for PCT/US2011/042639 mailed Mar. 13, 2012.

Written Opinion for PCT/US2011/042639 mailed Aug. 10, 2012.

PROCESS FOR PRODUCING ETHANOL USING A STACKED BED REACTOR

CROSS REFERENCE TO RELATED APPLICATIONS

This application is a continuation-in-part of U.S. application Ser. No. 13/094,714, filed Apr. 26, 2011, and a continuation-in-part of U.S. application Ser. No. 13/178,659, filed Jul. 8, 2011, both of which claims priority to U.S. Provisional App. No. 61/363,056, filed on Jul. 9, 2010, the entirety of which is incorporated herein by reference.

FIELD OF THE INVENTION

The present invention relates generally to processes for producing alcohol and, in particular, to forming an ethanol composition using a stacked bed reactor comprising a first catalyst comprising platinum and tin and a second catalyst comprising copper or an oxide thereof. In some embodiments, the second catalyst may further comprise zinc, aluminum, cobalt, or oxides thereof.

BACKGROUND OF THE INVENTION

Ethanol for industrial use is conventionally produced from organic feed stocks, such as petroleum oil, natural gas, or coal, from feed stock intermediates, such as syngas, or from starchy materials or cellulose materials, such as corn or sugar cane. Conventional methods for producing ethanol from organic feed stocks, as well as from cellulose materials, include the acid-catalyzed hydration of ethylene, methanol homologation, direct alcohol synthesis, and Fischer-Tropsch synthesis. Instability in organic feed stock prices contributes to fluctuations in the cost of conventionally produced ethanol, making the need for alternative sources of ethanol production all the greater when feed stock prices rise. Starchy materials, as well as cellulose materials, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds, including esters, has been widely studied, and a variety of combinations of catalysts, supports, and operating conditions have been mentioned in the literature.

More recently, even though it may not still be commercially viable it has been reported that ethanol can be produced from hydrogenating acetic acid using a cobalt catalyst at superatmospheric pressures such as about 40 to 120 bar, as described in U.S. Pat. No. 4,517,391.

On the other hand, U.S. Pat. No. 5,149,680 describes a process for the catalytic hydrogenation of carboxylic acids and their anhydrides to alcohols and/or esters utilizing a platinum group metal alloy catalyst. The catalyst is comprised of an alloy of at least one noble metal of Group VIII of the Periodic Table and at least one metal capable of alloying with the Group VIII noble metal, admixed with a component comprising at least one of the metals rhenium, tungsten or molybdenum. Although it has been claimed therein that improved selectivity to a mixture of alcohol and its ester with the unreacted carboxylic acid is achieved over the prior art references it was still reported that 3 to 9 percent of alkanes, such as methane and ethane are formed as by-products during the hydrogenation of acetic acid to ethanol under their optimal catalyst conditions.

A slightly modified process for the preparation of ethyl acetate by hydrogenating acetic acid has been reported in EP0372847. In this process, a carboxylic acid ester, such as for example, ethyl acetate is produced at a selectivity of greater than 50% while producing the corresponding alcohol at a selectivity less than 10% from a carboxylic acid or anhydride thereof by reacting the acid or anhydride with hydrogen at elevated temperature in the presence of a catalyst composition comprising as a first component at least one of Group VIII noble metal and a second component comprising at least one of molybdenum, tungsten and rhenium and a third component comprising an oxide of a Group IVB element. However, even the optimal conditions reported therein result in significant amounts of by-products including methane, ethane, acetaldehyde and acetone in addition to ethanol. In addition, the conversion of acetic acid is generally low and is in the range of about 5 to 40% except for a few cases in which the conversion reached as high as 80%.

Copper-iron catalysts for hydrogenolyzing esters to alcohols are described in U.S. Pat. No. 5,198,592. A hydrogenolysis catalyst comprising nickel, tin, germanium and/or lead is described in U.S. Pat. No. 4,628,130. A rhodium hydrogenolysis catalyst that also contains tin, germanium and/or lead is described in U.S. Pat. No. 4,456,775.

Several processes that produce ethanol from acetates, including methyl acetate and ethyl acetate, are known in the literature.

WO8303409 describes producing ethanol by carbonylation of methanol by reaction with carbon monoxide in the presence of a carbonylation catalyst to form acetic acid which is then converted to an acetate ester followed by hydrogenolysis of the acetate ester formed to give ethanol or a mixture of ethanol and another alcohol which can be separated by distillation. Preferably the other alcohol or part of the ethanol recovered from the hydrogenolysis step is recycled for further esterification. Carbonylation can be effected using a $CO/H_2$ mixture and hydrogenolysis can similarly be conducted in the presence of carbon monoxide, leading to the possibility of circulating gas between the carbonylation and hydrogenolysis zones with synthesis gas, preferably a 2:1 $H_2$:CO molar mixture being used as makeup gas.

WO2009063174 describes a continuous process for the production of ethanol from a carbonaceous feedstock. The carbonaceous feedstock is first converted to synthesis gas which is then converted to ethanoic acid, which is then esterified and hydrogenated to produce ethanol.

WO2009009320 describes an indirect route for producing ethanol. Carbohydrates are fermented under homoacidogenic conditions to form acetic acid. The acetic acid is esterified with a primary alcohol having at least 4 carbon atoms and hydrogenating the ester to form ethanol.

EP2060555 describes a process for producing ethanol where a carbonaceous feedstock is converted to synthesis gas which is converted to ethanoic acid, which is then esterified and which is then hydrogenated to produce ethanol. EP2072489 and EP2186787 also describe a similar process where the esters produced from esterification are fed to the alcohol synthesis reactor used to produce ethanol and methanol.

US Pub. No. 20110046421 describes a process for producing ethanol comprising converting carbonaceous feedstock to syngas and converting the syngas to methanol. Methanol is carbonylated to ethanoic acid, which is then subjected to a two stage hydrogenation process. First the ethanoic acid is converted to ethyl ethanoate followed by a secondary hydrogenation to ethanol.

US Pub. No. 20100273229 describes a process for producing acetic acid intermediate from carbohydrates, such as corn, using enzymatic milling and fermentation steps. The acetic acid intermediate is acidified with calcium carbonate and the acetic acid is esterified to produce esters. Ethanol is produced by a hydrogenolysis reaction of the ester.

U.S. Pat. No. 5,414,161 describes a process for producing ethanol by a gas phase carbonylation of methanol with carbon monoxide followed by a hydrogenation. The carbonylation produces acetic acid and methyl acetate, which are separated and the methyl acetate is hydrogenated to produce ethanol in the presence of a copper-containing catalyst.

U.S. Pat. No. 4,497,967 describes a process for producing ethanol from methanol by first esterifying the methanol with acetic acid. The methyl acetate is carbonylated to produce acetic anhydride which is then reacted with one or more aliphatic alcohols to produce acetates. The acetates are hydrogenated to produce ethanol. The one or more aliphatic alcohols formed during hydrogenation are returned to the acetic anhydride esterification reaction.

U.S. Pat. No. 4,454,358 describes a process for producing ethanol from methanol. Methanol is carbonylated to produce methyl acetate and acetic acid. The methyl acetate is recovered and hydrogenated to produce methanol and ethanol. Ethanol is recovered by separating the methanol/ethanol mixture. The separated methanol is returned to the carbonylation process.

The need remains for improved processes for efficient ethanol production by reducing esters on a commercially feasible scale.

SUMMARY OF THE INVENTION

In a first embodiment, the present invention is directed to a process for producing ethanol comprising the steps of introducing a feed stream and hydrogen into a stacked bed reactor that comprises a first bed and a second bed to produce a crude ethanol product, wherein the first bed comprises a first catalyst on a first support and the second bed comprises a second catalyst comprising copper or an oxide thereof on a second support, and recovering ethanol from the crude ethanol product in one or more columns. In one embodiment, the first catalyst comprises platinum and tin on a first support. In one embodiment, the second catalyst preferably further comprises zinc, aluminum, cobalt, or oxides thereof.

In a second embodiment, the present invention is directed to a process for producing ethanol comprising the steps of introducing hydrogen and a feed stream comprising from 5 to 40 wt. % ethyl acetate and 60 to 95 wt. % acetic acid into a stacked bed reactor to produce a crude ethanol product. The stacked bed reactor comprises a first bed and a second bed. The first bed comprises a first catalyst comprising platinum and tin on a first support comprising a support modifier selected from the group consisting of $WO_3$, $MoO_3$, $Fe_2O_3$, $Cr_2O_3$, $Nb_2O_5$, $V_2O_5$, $MnO_2$, $CuO$, $Co_2O_3$, and $Bi_2O_3$, and the second bed comprises a second catalyst comprising copper or an oxide thereof on a second support. The process further involves recovering ethanol from the crude ethanol product in one or more columns.

In another embodiment, the present invention is directed to a process for producing ethanol comprising the steps of introducing hydrogen and a feed stream comprising from 5 to 40 wt. % ethyl acetate and 60 to 95 wt. % acetic acid into a stacked bed reactor to produce a crude ethanol product. The stacked bed reactor comprises a first bed and a second bed. The feed stream is fed to the first bed to yield a reactor stream comprising ethyl acetate and ethanol that is fed to the second bed to yield the ethanol product.

In a third embodiment, the present invention is directed to a process for producing ethanol comprising the steps of introducing hydrogen and a feed stream into a stacked bed reactor that comprises a first bed and a second bed to produce a crude ethanol product, wherein the first bed comprises a first catalyst comprising platinum and tin on a first support, and the second bed comprises a second catalyst comprising copper or an oxide thereof on a second support, and wherein the first support and second support each comprise alumina, and recovering ethanol from the crude ethanol product in one or more columns.

In a fourth embodiment, the present invention is directed to a process for producing ethanol comprising the steps of introducing hydrogen and a feed stream into a stacked bed reactor that comprises a first bed and a second bed to produce a crude ethanol product, wherein the first bed has a bed volume that is larger than the second bed, wherein the first bed comprises a first catalyst, and the second bed comprises a second catalyst that is different than the first catalyst, and recovering ethanol from the crude ethanol product in one or more columns. In one embodiment, acetic acid conversion in the first bed is greater than 97%. A high conversion allows a low acetic acid concentration to be fed to the second bed, preferably less than 3 wt. %. In one embodiment, the bed volume of the first bed is at least twice as large as the second bed.

BRIEF DESCRIPTION OF DRAWINGS

The invention may be more completely understood in consideration of the following detailed description of various embodiments of the invention in connection with the accompanying drawings, wherein like numerals designate similar parts.

DETAILED DESCRIPTION OF THE INVENTION

Figure 1:
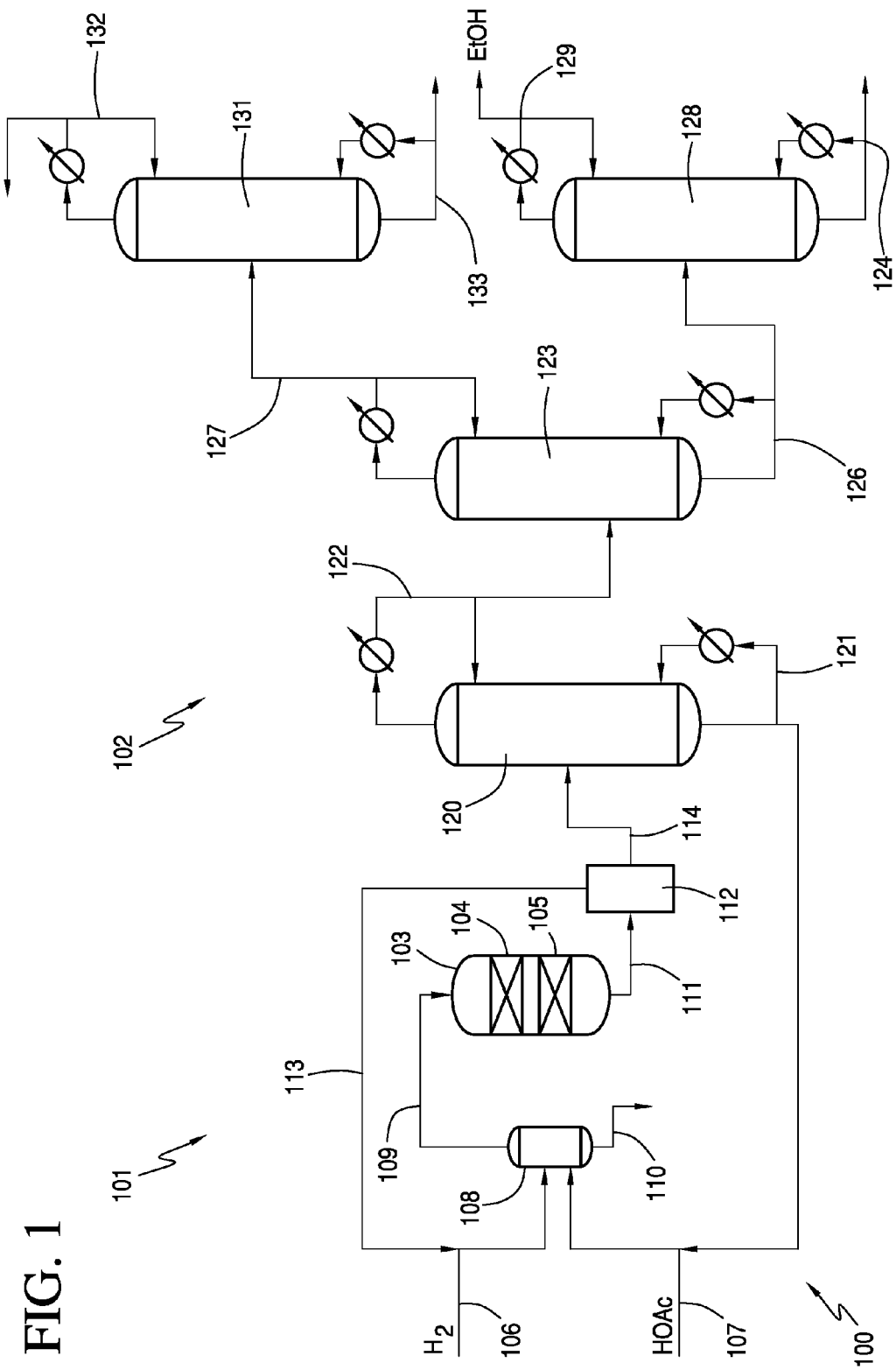
FIG. 1 is a schematic diagram of a hydrogenation process having a stacked bed reactor and four columns in accordance with an embodiment of the present invention.

The present invention relates generally to processes for forming ethanol using a stacked bed reactor. For purposes of the present invention, a stacked bed reactor comprises at least two different catalysts. Each catalyst may be a hydrogenation catalyst capable of reducing a carboxylic acid or ester thereof to an alcohol. Preferably, the stacked bed reactor comprises two or more beds. In each additional bed there may be an additional hydrogenation catalyst.

In one embodiment, the first bed may have a greater bed volume than the other beds, and, preferably, the bed volume of the first bed may be at least twice as large as the other beds, and more preferably at least 2.2 times larger or at least 2.3 times larger. A large bed may provide for very high conversions of acetic acid, e.g., greater than 97%, greater than 98% or greater than 99%. In one embodiment reaction stream from the first bed contains very low concentrations of acetic acid, e.g., less than 3 wt. %, or less than 2 wt. % or less than 0.5 wt. %. In some embodiments, the reaction stream from the first bed may be substantially free of acetic acid. Without being bound by theory, a larger first bed may ensure that substantially all of the acetic acid is consumed and thus the amount of acetic acid fed to the second bed is reduced. The second bed may comprise a copper catalyst that may become less stable and lose catalytic activity in the presence of acetic acid and/or water. Reducing the amount of acetic acid that is fed to the second bed that contains the copper catalyst may improve the conversion of ethyl acetate to ethanol.

A feed stream that comprises acetic acid and/or ethyl acetate may be fed to the stacked bed reactor. In one embodiment, acetic acid may be converted in the first bed. Acetic acid may be converted to ethanol and/or ethyl acetate. In the second bed, ethyl acetate may be converted, preferably to ethanol. Preferably, ethyl acetate is converted to ethanol in the second bed in the absence of acetic acid.

A problem feeding a mixed stream of acetic acid and ethyl acetate is that catalysts for converting acetic acid may not convert the ethyl acetate in the feed. Without converting ethyl acetate, the feed to the reactor must contain very low amounts of ethyl acetate and ethyl acetate must be purged from the process when recovering ethanol. In addition, catalysts that are active for converting ethyl acetate to ethanol, the catalysts may be deactivated by the presence of acetic acid or water. Deactivation of the catalyst causes a decrease in performance so the amount of acetic acid in the reaction mixture needs to be reduced before the mixture is exposed to the ethyl acetate converting catalyst.

Embodiments of the present invention provide advantageous solutions to these problems to provide for effective ethanol production. When mixed feeds, i.e. feeds containing acetic acid and ethyl acetate, are fed to the first bed, the catalyst is preferably suited to converting both acetic acid and ethyl acetate. Generally, acetic acid conversion may be higher than ethyl acetate conversion. In addition, the reactor stream passes from the first bed to the second bed without any purges of acetic acid or separation of the reactor stream. In one embodiment, hydrogen is fed, preferably in excess to the first bed, and any remaining hydrogen passes along in the reactor stream to the second bed. Although it is preferred to reduce the acetic acid fed to the second bed, in some embodiments, the process may convert ethyl acetate at higher rates than acetic acid in the second bed in the presence of acetic acid. This allows the process of the present invention to efficiently produce ethanol from acetic acid.

In one embodiment, the feed stream is a mixed feed comprising both acetic acid and ethyl acetate. Preferably, the mixed feed comprises from 5 to 40 wt. % ethyl acetate and from 60 to 95 wt. % acetic acid, and more preferably from 10 to 30 wt. % ethyl acetate and 70 to 90 wt. % acetic acid. In one embodiment, the mixed feed comprises 30 wt. % ethyl acetate and 70 wt. % acetic acid. In another embodiment, the mixed feed comprises 15 wt. % ethyl acetate and 85 wt. % acetic acid. In still another embodiment, the mixed feed comprises 5 wt. % ethyl acetate and 95 wt. % acetic acid.

Using a mixed feed, the hydrogenation in the stacked bed reactor may achieve favorable conversion of acetic acid and ethyl acetate. For the purposes of the present invention, the term "conversion" refers to the net change of the flow of acetic acid or ethyl acetate into the multiple bed reactor as compared to the flow of acetic acid or ethyl acetate out of the stacked bed reactor. The net change may represent that the acetic acid and/or ethyl acetate are converted to a compound other than acetic acid or ethyl acetate, respectively. Conversion is expressed as a percentage based on acetic acid and/or ethyl acetate in the feed. The conversion of acetic acid in the first bed may be at least 60%, at least 70% or at least 80%. In some embodiments, a larger bed volume for the first bed may achieve an acetic acid conversion that is greater than 97%, 98%, or 99%. Generally, acetic acid is not converted in the second bed, and thus the conversion in the first bed is representative of the conversion of acetic acid in the stacked bed reactor. The conversion of ethyl acetate in the first bed preferably is greater than 0%, meaning that more ethyl acetate is consumed than produced. During the hydrogenation of acetic acid in the first bed, ethyl acetate may be produced and further converted in the second bed to ethanol. Thus, negative conversions of ethyl acetate, i.e. conversions less than 0%, may be tolerated in the first bed provided that the second bed converts the ethyl acetate to ethanol and there is no net increase of ethyl acetate across the stacked bed. Thus the conversion of ethyl acetate in the stacked bed reactor is greater than 0%, e.g., greater than 5%, greater than 25%, or greater than 50%. In an exemplary embodiment, the conversion of ethyl acetate in the second bed may range from 50 to 98%, e.g., from 60 to 95% or from 70 to 90%.

In one aspect, the mixed feed is converted to ethanol and ethyl acetate. Preferably, the selectivity to ethanol is greater than ethyl acetate and the reactor stream from the first reactor bed contains lower ethyl acetate concentrations than the feed stream, based on weight. Thus, the second reactor bed may react the remaining ethyl acetate while allowing a majority of the ethanol to pass through.

In another aspect, the mixed feed is converted mainly to ethyl acetate with low ethanol concentrations, based on weight. In these embodiments, the second reactor bed may be used to convert the ethyl acetate to ethanol.

In one embodiment, the feed stream may comprise essentially acetic acid. Preferably the acetic acid concentration is greater than 95 wt. %, greater than 97 wt. % or greater than 99 wt. %. In these embodiments, the feed stream may be referred to as an acetic acid feed stream. The acetic acid feed stream may comprise other organics, including aldehydes, ketones, and esters. Preferably for such embodiments, the acetic acid feed stream may be substantially free of ethyl acetate. The conversion of the acetic acid feed stream may be at least 60%, at least 70% or at least 80%. In some embodiments, acetic acid is converted to ethanol and ethyl acetate. In other embodiments, acetic acid is converted mainly to ethyl acetate.

The mixed feed or acetic acid feed stream is fed to a first bed. In one embodiment, hydrogen may also be supplied to the first bed. In one embodiment, the first bed comprises a first catalyst comprising platinum and tin on a first support. Platinum may be present in the catalyst in an amount from 0.1 to 10 wt. %, e.g. from 0.1 to 5 wt. %, or from 0.1 to 3 wt. %. Tin may be present in an amount from 0.1 to 20 wt. %, e.g., from 0.1 to 10 wt. %, or from 0.1 to 5 wt. %.

The first catalyst may also comprise one or more third metals selected from the group consisting of cobalt, vanadium, tungsten, palladium, lanthanum, cesium, manganese, ruthenium, rhenium, gold, and nickel. More preferably, the one or more third metals are selected from the group consisting of cobalt, vanadium, palladium, and cesium. In one embodiment, the first catalyst is substantially free of rhenium, tungsten, and/or molybdenum. The third metal, when present, may be present in the catalyst in an amount from 0.05 to 5 wt.

%, e.g. from 0.1 to 5 wt. %, or from 0.1 to 3 wt. %. Suitable metal combinations with the third metals may include platinum/tin/palladium, platinum/tin/cobalt, platinum/tin/cesium, platinum/tin/palladium/cobalt, and platinum/tin/palladium/cesium.

The first catalysts of the present invention may be on any suitable support material. In one embodiment, the support material may be an inorganic oxide. In one embodiment, the support material may be selected from the group consisting of silica, silica/alumina, calcium metasilicate, pyrogenic silica, high purity silica, carbon, activated carbon, alumina, titiana, zirconia, graphite, zeolites, and mixtures thereof. Zeolites may include high silica zeolites (HSZ™ Tosoh Products) that contain more silica than alumina. Silica gel may be used as a precursor for preparing silica containing supports. Preferably, the support material comprises silica, or silica/alumina. In one embodiment the first catalyst preferably does not contain a zeolite support. In preferred embodiments, the support material for the first catalyst is present in an amount from 25 wt. % to 99 wt. %, e.g., from 30 wt. % to 98 wt. % or from 35 wt. % to 95 wt. %.

The surface area of silicaceous support material, e.g., silica, preferably is at least 50 m$^2$/g, e.g., at least 100 m$^2$/g, at least 150 m$^2$/g, at least 200 m$^2$/g or most preferably at least 250 m$^2$/g. In terms of ranges, the silicaceous support material preferably has a surface area from 50 to 600 m$^2$/g, e.g., from 100 to 500 m$^2$/g or from 100 to 300 m$^2$/g. High surface area silica, as used throughout the application, refers to silica having a surface area of at least 250 m$^2$/g. For purposes of the present specification, surface area refers to BET nitrogen surface area, meaning the surface area as determined by ASTM D6556-04, the entirety of which is incorporated herein by reference.

The silicaceous support material also preferably has an average pore diameter from 5 to 100 nm, e.g., from 5 to 30 nm, from 5 to 25 nm or from about 5 to 10 nm, as determined by mercury intrusion porosimetry, and an average pore volume from 0.5 to 2.0 cm$^3$/g, e.g., from 0.7 to 1.5 cm$^3$/g or from about 0.8 to 1.3 cm$^3$/g, as determined by mercury intrusion porosimetry.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the silicaceous support material has a morphology that allows for a packing density from 0.1 to 1.0 g/cm$^3$, e.g., from 0.2 to 0.9 g/cm$^3$ or from 0.5 to 0.8 g/cm$^3$. In terms of size, the silica support material preferably has an average particle size, e.g., meaning the diameter for spherical particles or equivalent spherical diameter for non-spherical particles, from 0.01 to 1.0 cm, e.g., from 0.1 to 0.5 cm or from 0.2 to 0.4 cm. Since the one or more active metal(s) that are disposed on or within the support are generally very small in size, those active metals should not substantially impact the size of the overall catalyst particles. Thus, the above particle sizes generally apply to both the size of the support as well as to the final catalyst particles.

A preferred silica support material is SS61138 High Surface Area (HSA) Silica Catalyst Carrier from Saint-Gobain NorPro. The Saint-Gobain NorPro SS61138 silica contains approximately 95 wt. % high surface area silica; a surface area of about 250 m$^2$/g; a median pore diameter of about 12 nm; an average pore volume of about 1.0 cm$^3$/g as measured by mercury intrusion porosimetry and a packing density of about 0.352 g/cm$^3$.

A preferred silica/alumina support material is KA-160 (Süd Chemie) silica spheres having a nominal diameter of about 5 mm, a density of about 0.562 g/ml, in absorptivity of about 0.583 g H$_2$O/g support, a surface area of about 160 to 175 m$^2$/g, and a pore volume of about 0.68 ml/g.

The support material for the first catalyst may also comprise a support modifier. A support modifier may adjust the acidity of the support material. In one embodiment, the total weight of the support modifiers are present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst.

Support modifiers may adjust the acidity of the support for the first catalyst. For example, the acid sites, e.g. Brønsted acid sites, on the support material may be adjusted by the support modifier to favor selectivity to ethanol during the hydrogenation of acetic acid. The acidity of the support material may be adjusted by reducing the number or reducing the availability of Brønsted acid sites on the support material. The support material may also be adjusted by having the support modifier change the pKa of the support material. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference. In particular, the use of modified supports that adjusts the acidity of the support to make the support less acidic or more basic favors formation of ethanol over other hydrogenation products.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIII metals, aluminum oxides, and mixtures thereof. Acidic support modifiers include those selected from the group consisting of TiO$_2$, ZrO$_2$, Nb$_2$O$_5$, Ta$_2$O$_5$, Al$_2$O$_3$, B$_2$O$_3$, P$_2$O$_5$, and Sb$_2$O$_3$. Preferred acidic support modifiers include those selected from the group consisting of TiO$_2$, ZrO$_2$, Nb$_2$O$_5$, Ta$_2$O$_5$, and Al$_2$O$_3$. The acidic modifier may also include those selected from the group consisting of WO$_3$, MoO$_3$, Fe$_2$O$_3$, Cr$_2$O$_3$, V$_2$O$_5$, MnO$_2$, CuO, Co$_2$O$_3$, and Bi$_2$O$_3$.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate (CaSiO$_3$). If the basic support modifier comprises calcium metasilicate, it is preferred that at least a portion of the calcium metasilicate is in crystalline form.

The reactants, either the mixed feed or acetic acid feed stream, pass through the first bed containing the first catalyst to produce a reactor stream. Hydrogen preferably passes through the first bed in the reactor stream so that it may be consumed in the second bed. In one embodiment, there is no separate hydrogen feed to the second bed. Depending on the selectivity, the reactor stream may comprise ethanol and ethyl acetate or mainly ethyl acetate. The reactor stream is passed over the second bed that contains the second catalyst. It should be understood that a reactor may have one or more first beds and one or more second beds. Preferably, in the stacked bed reactor, the first and second beds are adjacent such that the reactor stream from the first bed passes directly into the second bed.

The second bed may comprise a second catalyst that comprises copper or an oxide thereof. In one embodiment, the second catalyst may further comprise zinc, aluminum, cobalt, or oxides thereof. In some stacked beds of the present invention, to achieve suitable ethyl acetate conversion and favorable ethanol selectivity, it is preferred that the second catalyst comprises copper and zinc or an oxide thereof. Copper may be present in an amount from 35 to 70 wt. % and more preferably 40 to 65 wt. %. Zinc may be present in an amount from 15 to 40 wt. % and more preferably 20 to 30 wt. %. Copper and zinc may be present as oxides. In one embodiment, the second catalyst comprises greater than 65 wt. % copper and greater than 25 wt. % zinc. In another embodiment, the second catalyst comprises 41 wt. % copper and 26 wt. % zinc. In still another embodiment, the second catalyst comprises 60.8 wt. % copper and 28.8 wt. % zinc. The second catalyst may also comprise a third metal selected from the group consisting of molybdenum, tin, iron, cobalt, vanadium, tungsten, palladium, platinum, lanthanum, cerium, manganese, ruthenium, rhenium, gold, and nickel. Preferably the third metal is not chromium and the second catalyst may be substantially free of chromium.

The second catalysts of the present invention may be on any suitable support material. In one embodiment, the support material may be an inorganic oxide. In one embodiment, the support material may be selected from the group consisting of silica, silica/alumina, alumina, titania, zeolites, and mixtures thereof. Preferably, the support material for the second catalyst comprises silica/alumina or alumina. In preferred embodiments, the support material for the second catalyst is present in an amount from 1 wt. % to 50 wt. %, e.g., from 1 wt. % to 30 wt. % or from 5 wt. % to 15 wt. %. In one embodiment, the support material for the first and second catalysts may both comprise alumina.

For purposes of the present invention, the second catalyst is capable of converting ethyl acetate in the presence of acetic acid. Thus, the first reactor bed does not need to achieve complete conversion of acetic acid and also there is no separate purge of acetic acid between the first and second bed. In one embodiment, the reactor stream from the first bed may comprise less than 70 wt. % acetic acid, e.g., at less than 40 wt. % acetic acid or less than 20 wt. % acetic acid. In one embodiment, the reactor stream may comprise at least 5 wt. % acetic acid, e.g., at least 10 wt. % acetic acid or at least 15 wt. % acetic acid.

In one embodiment, both the first and second beds may be in one vessel. In other embodiments, the stacked bed reactor may comprise separate vessels, each containing a first or second bed. The catalyst loading in the first and second bed may vary. In terms of a volumetric ratio the first bed may contain more catalyst than the second bed, e.g., greater than 1.5:1, or greater than 2:1. In many embodiments of the present invention, an "adiabatic" stacked bed reactor may be used; that is, there is little or no need for internal plumbing through the reaction zone to add or remove heat.

The hydrogenation in the stacked bed reactor may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 hr$^{-1}$, e.g., greater than 1000 hr$^{-1}$, greater than 2500 hr$^{-1}$ or even greater than 5000 hr$^{-1}$. In terms of ranges the GHSV may range from 50 hr$^{-1}$ to 50,000 hr$^{-1}$, e.g., from 500 hr$^{-1}$ to 30,000 hr$^{-1}$, from 1000 hr$^{-1}$ to 10,000 hr$^{-1}$, or from 1000 hr$^{-1}$ to 6500 hr$^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 hr$^{-1}$ or 6,500 hr$^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

Selectivity is expressed as a mole percent based on converted acetic acid and/or ethyl acetate fed to the first reactor bed. It should be understood that each compound converted from acetic acid and/or ethyl acetate has an independent selectivity and that selectivity is independent from conversion. For example, if 60 mole % of the converted acetic acid is converted to ethanol, we refer to the ethanol selectivity as 60%. Total selectivity is based on the combined converted acetic acid and ethyl acetate. Preferably, the catalyst total selectivity to ethanol is at least 60%, e.g., at least 70%, or at least 80%. Preferably, the total selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

In one embodiment, when an acetic acid stream is fed to the stacked bed reactor, the overall selectivity to methyl acetate is less than 5%, e.g., less than 3% or more preferably less than 2%. In one embodiment, substantially no methyl acetate is formed in the stacked bed reactor.

The term "productivity," as used herein, refers to the grams of a specified product, ethanol, formed during the hydrogenation based on the kilograms of catalyst used per hour. For purposes of the present invention, productivity includes both the first and second catalyst. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise ethanol and water. Exemplary compositional ranges for the crude ethanol product are provided in Table 1. The "others" identified in Table 1 may include, for example, esters, ethers, aldehydes, ketones, alkanes, higher alcohols, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product comprises acetic acid in an amount less than 20 wt. %, e.g., less than 15 wt. %, less than 10 wt. % or less than 5 wt. %. In terms of ranges, the acetic acid concentration of Table 1 may range from 0.1 wt. % to 20 wt. %, e.g., 0.2 wt. % to 15 wt. %, from 0.5 wt. % to 10 wt. % or from 1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from other available carbon source. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum,* and *Bacteriodes,* and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also US Publ. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by converting carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

Depending on the crude ethanol product composition from the stacked reactor bed, there may be several different processes for separating the impurities and recovering ethanol. FIGS. 1-5 illustrate various separation schemes for recovering ethanol. The hydrogenation system 100 in FIGS. 1-5 comprises reaction zone 101 and separation zone 102. Reaction zone comprises a stacked bed reactor 103 having a first bed 104 and a second bed 105. First bed 104 comprises a first catalyst comprising platinum and tin as described above. Second bed 105 comprises second catalyst comprising copper or oxides thereof, as described above.

Hydrogen in line 106 and a reactant feed line 107 are fed to a vaporizer 108 to create a vapor feed stream in line 109 that is directed to stacked bed reactor 103. Hydrogen feed line 106 may be preheated to a temperature from 30° C. to 150° C., e.g., from 50° C. to 125° C. or from 60° C. to 115° C. Hydrogen feed line 106 may be fed at a pressure from 1300 kPa to 3100 kPa, e.g., from 1500 kPa to 2800 kPa, or 1700 kPa to 2600 kPa. Reactant in line 107 may comprise acetic acid and/or ethyl acetate. In one embodiment, reactant in line 107 comprises greater than 95 wt. % acetic acid. In another embodiment, reactant in line 107 comprises from 5 to 40 wt. % ethyl acetate and 60 to 95 wt. % acetic acid, and more preferably from 5 to 30 wt. % ethyl acetate and 70 to 95 wt. % acetic acid. The acetic acid and/or ethyl acetate may be recycled from within system 100 or is fresh. In one embodiment, lines 106 and 107 may be combined and jointly fed to vaporizer 108 to form a vapor feed stream in line 109. The temperature of vapor feed stream in line 109 is preferably from 100° C. to 350° C., e.g., from 120° C. to 310° C. or from 150° C. to 300° C. Any feed that is not vaporized is removed from vaporizer 108 in blowdown stream 110 and may be recycled or discarded thereto. The mass ratio of vapor feed stream in line 109 to blowdown stream 110 may be from 6:1 to 500:1, e.g., from 10:1 to 500:1, from 20:1 to 500:1 or from 50:1 to 500:1. In addition, although vapor feed stream in line 109 is shown as being directed to the top of stacked bed reactor 103, line 109 may be directed to the side, upper portion, or bottom. More preferably, vapor feed stream in line 109 is fed to the first bed 104.

In one embodiment, one or more guard beds (not shown) may be used upstream of the reactor, optionally upstream of vaporizer 108, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens.

In reactor 103, acetic acid and/or ethyl acetate is preferably reacted in first bed 104 and the reactor stream from first bed 104 is passed along to second bed 105. In second bed 105, the ethyl acetate is preferably reduced to ethanol. During the hydrogenation process, a crude ethanol product stream is withdrawn, preferably continuously, from reactor 103 via line 111.

The crude ethanol product stream in line 111 may be condensed and fed to a separator 112, which, in turn, provides a vapor stream 113 and a liquid stream 114. In some embodiments, separator 112 may comprise a flasher or a knockout pot. Separator 112 may operate at a temperature from 20° C. to 250° C., e.g., from 30° C. to 225° C. or from 60° C. to 200° C. The pressure of separator 112 may be from 50 kPa to 2000 kPa, e.g., from 75 kPa to 1500 kPa or from 100 kPa to 1000 kPa. Optionally, the crude ethanol product in line 111 may pass through one or more membranes to separate hydrogen and/or other non-condensable gases.

The vapor stream 113 exiting separator 112 may comprise hydrogen and hydrocarbons, and may be purged and/or returned to reaction zone 101. When returned to reaction zone 101, vapor stream 113 is combined with the hydrogen feed 106 and co-fed to vaporizer 108. In some embodiments, the returned vapor stream 113 may be compressed before being combined with hydrogen feed 106.

In FIG. 1, the liquid stream 114 from separator 112 is withdrawn and introduced in the lower part of first column 120, e.g., lower half or lower third. First column 120 is also referred to as an "acid separation column." In one embodiment, the contents of liquid stream 114 are substantially similar to the crude ethanol product obtained from the reactor, except that the composition has been depleted of hydrogen, carbon dioxide, methane and/or ethane, which are removed by separator 112. Accordingly, liquid stream 114 may also be referred to as a crude ethanol product. Exemplary components of liquid stream 114 are provided in Table 2. It should be understood that liquid stream 114 may contain other components, not listed in Table 2.

TABLE 2

COLUMN FEED COMPOSITION
(Liquid Stream 114)

| | Conc. (wt. %) | Conc. (wt. %) | Conc. (wt. %) |
|---|---|---|---|
| Ethanol | 5 to 72 | 10 to 70 | 15 to 65 |
| Acetic Acid | <90 | 0 to 50 | 0 to 35 |
| Water | 5 to 30 | 5 to 28 | 10 to 26 |
| Ethyl Acetate | <30 | 0.001 to 20 | 1 to 12 |
| Acetaldehyde | <10 | 0.001 to 3 | 0.1 to 3 |
| Acetals | 0.01 to 10 | 0.01 to 6 | 0.01 to 5 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout the present specification are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol, 2-butanol or mixtures thereof. In one embodiment, the liquid stream 114 may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

Optionally, crude ethanol product in line 111 or in liquid stream 114 may be further fed to an esterification reactor, hydrogenolysis reactor, or combination thereof. An esterification reactor may be used to consume residual acetic acid present in the crude ethanol product to further reduce the amount of acetic acid that would otherwise need to be removed. Hydrogenolysis may be used to convert ethyl acetate in the crude ethanol product to ethanol.

In the embodiment shown in FIG. 1, line 114 is introduced in the lower part of first column 120, e.g., lower half or lower third. In first column 120, unreacted acetic acid, a portion of the water, and other heavy components, if present, are removed from the composition in line 121 and are withdrawn, preferably continuously, as residue. Some or all of the residue may be returned and/or recycled back to reaction zone 101 via line 121. Recycling the acetic acid in line 121 to the vaporizer 108 may reduce the amount of heavies that need to be purged from vaporizer 108. Optionally, at least a portion of residue in line 121 may be purged from the system. Reducing the amount of heavies to be purged may improve efficiencies of the process while reducing byproducts.

First column 120 also forms an overhead distillate, which is withdrawn in line 122, and which may be condensed and refluxed, for example, at a ratio from 10:1 to 1:10, e.g., from 3:1 to 1:3 or from 1:2 to 2:1.

When column 120 is operated under standard atmospheric pressure, the temperature of the residue exiting in line 121 preferably is from 95° C. to 120° C., e.g., from 110° C. to 117° C. or from 111° C. to 115° C. The temperature of the distillate exiting in line 122 preferably is from 70° C. to 110° C., e.g., from 75° C. to 95° C. or from 80° C. to 90° C. Column 120 preferably operates at ambient pressure. In other embodiments, the pressure of first column 120 may range from 0.1 kPa to 510 kPa, e.g., from 1 kPa to 475 kPa or from 1 kPa to 375 kPa. Exemplary components of the distillate and residue compositions for first column 120 are provided in Table 3 below. It should also be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

ACID COLUMN 120 (FIG. 1)

| | Conc. (wt. %) | Conc. (wt. %) | Conc. (wt. %) |
|---|---|---|---|
| Distillate | | | |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |
| Acetals | 0.01 to 10 | 0.05 to 6 | 0.1 to 5 |
| Acetone | <0.05 | 0.001 to 0.03 | 0.01 to 0.025 |
| Residue | | | |
| Acetic Acid | 60 to 100 | 70 to 95 | 85 to 92 |
| Water | <30 | 1 to 20 | 1 to 15 |
| Ethanol | <1 | <0.9 | <0.07 |

As shown in Table 3, without being bound by theory, it has surprisingly and unexpectedly been discovered that when any amount of acetal is detected in the feed that is introduced to the acid separation column 120, the acetal appears to decompose in the column such that less or even no detectable amounts are present in the distillate and/or residue.

The distillate in line 122 preferably comprises ethanol, ethyl acetate, and water, along with other impurities, which may be difficult to separate due to the formation of binary and tertiary azeotropes. To further separate distillate, line 122 is introduced to the second column 123, also referred to as the "light ends column," preferably in the middle part of column 123, e.g., middle half or middle third. Preferably the second column 123 is an extractive distillation column. In such embodiments, an extraction agent, such as water, may be added to second column 123. If the extraction agent comprises water, it may be obtained from an external source or from an internal return/recycle line from one or more of the other columns.

The molar ratio of the water in the extraction agent to the ethanol in the feed to the second column is preferably at least 0.5:1, e.g., at least 1:1 or at least 3:1. In terms of ranges, preferred molar ratios may range from 0.5:1 to 8:1, e.g., from 1:1 to 7:1 or from 2:1 to 6.5:1. Higher molar ratios may be used but with diminishing returns in terms of the additional ethyl acetate in the second distillate and decreased ethanol concentrations in the second column residue.

In one embodiment, an additional extraction agent, such as water from an external source, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N-dimethyl-1,3-propanediamine, N,N'-dimethylethylenediamine, diethylene triamine, hexamethylene diamine and 1,3-diaminopentane, an alkylated thiopene, dodecane, tridecane, tetradecane and chlorinated paraffins, may be added to second column 123. Some suitable extraction agents include those described in U.S. Pat. Nos. 4,379,028, 4,569,726, 5,993,610 and 6,375,807, the entire contents and disclosure of which are hereby incorporated by reference.

In the embodiments of the present invention, without the use of an extractive agent, a larger portion of the ethanol would carry over into the second distillate in line 127. By using an extractive agent in second column 123, the separation of ethanol into the second residue in line 126 is facilitated thus increasing the yield of the overall ethanol product in the second residue in line 126.

Second column 123 may be a tray or packed column. In one embodiment, second column 123 is a tray column having from 5 to 70 trays, e.g., from 15 to 50 trays or from 20 to 45 trays. Although the temperature and pressure of second column 123 may vary, when at atmospheric pressure the temperature of the second residue exiting in line 126 preferably is from 60° C. to 90° C., e.g., from 70° C. to 90° C. or from 80° C. to 90° C. The temperature of the second distillate exiting in line 127 from second column 123 preferably is from 50° C. to 90° C., e.g., from 60° C. to 80° C. or from 60° C. to 70° C. Column 123 may operate at atmospheric pressure. In other embodiments, the pressure of second column 123 may range from 0.1 kPa to 510 kPa, e.g., from 1 kPa to 475 kPa or from 1 kPa to 375 kPa. Exemplary components for the distillate and residue compositions for second column 123 are provided in Table 4 below. It should be understood that the distillate and residue may also contain other components, not listed, such as components in the feed.

TABLE 4

SECOND COLUMN 123 (FIG. 1)

| | Conc. (wt. %) | Conc. (wt. %) | Conc. (wt. %) |
|---|---|---|---|
| Distillate | | | |
| Ethyl Acetate | 10 to 99 | 25 to 95 | 50 to 93 |
| Acetaldehyde | <25 | 0.5 to 15 | 1 to 8 |
| Water | <25 | 0.5 to 20 | 4 to 16 |
| Ethanol | <30 | 0.001 to 15 | 0.01 to 5 |
| Acetal | 0.01 to 20 | 1 to 20 | 5 to 20 |
| Residue | | | |
| Water | 30 to 90 | 40 to 85 | 50 to 85 |
| Ethanol | 10 to 75 | 15 to 60 | 20 to 50 |
| Ethyl Acetate | <3 | 0.001 to 2 | 0.001 to 0.5 |
| Acetic Acid | <0.5 | 0.001 to 0.3 | 0.001 to 0.2 |

In preferred embodiments, the recycling of the third residue promotes the separation of ethyl acetate from the residue of the second column 123. For example, the weight ratio of ethyl acetate in the second residue to second distillate preferably is less than 0.4:1, e.g., less than 0.2:1 or less than 0.1:1. In embodiments that use an extractive distillation column with water as an extraction agent as the second column 123, the weight ratio of ethyl acetate in the second residue to ethyl acetate in the second distillate approaches zero. Second residue may comprise, for example, from 30% to 99.5% of the water and from 85 to 100% of the acetic acid from line 122. The second distillate in line 127 comprises ethyl acetate and additionally comprises water, ethanol, and/or acetaldehyde.

The weight ratio of ethanol in the second residue to second distillate preferably is at least 3:1, e.g., at least 6:1, at least 8:1, at least 10:1 or at least 15:1. All or a portion of the third residue is recycled to the second column. In one embodiment, all of the third residue may be recycled until process 100 reaches a steady state and then a portion of the third residue is recycled with the remaining portion being purged from the system 100. The composition of the second residue will tend to have lower amounts of ethanol than when the third residue is not recycled. As the third residue is recycled, the composition of the second residue, as provided in Table 4, comprises less than 30 wt. % of ethanol, e.g., less than 20 wt. % or less than 15 wt. %. The majority of the second residue preferably comprises water. Notwithstanding this effect, the extractive distillation step advantageously also reduces the amount of ethyl acetate that is sent to the third column, which is highly beneficial in ultimately forming a highly pure ethanol product.

As shown, the second residue from second column 123, which comprises ethanol and water, is fed via line 126 to third column 128, also referred to as the "product column." More preferably, the second residue in line 126 is introduced in the lower part of third column 128, e.g., lower half or lower third. Third column 128 recovers ethanol, which preferably is substantially pure with respect to organic impurities and other than the azeotropic water content, as the distillate in line 129. The distillate of third column 128 preferably is refluxed as shown in FIG. 1, for example, at a reflux ratio from 1:10 to 10:1, e.g., from 1:3 to 3:1 or from 1:2 to 2:1. The third residue in line 124, which comprises primarily water, preferably is returned to the second column 123 as an extraction agent as described above. In one embodiment (not shown), a first portion of the third residue in line 124 is recycled to the second column and a second portion is purged and removed from the system. In one embodiment, once the process reaches steady state, the second portion of water to be purged is substantially similar to the amount water formed in the hydrogenation of acetic acid. In one embodiment, a portion of the third residue may be used to hydrolyze any other stream, such as one or more streams comprising ethyl acetate.

Third column 128 is preferably a tray column as described above and operates at atmospheric pressure or optionally at pressures above or below atmospheric pressure. The temperature of the third distillate exiting in line 129 preferably is from 50° C. to 110° C., e.g., from 70° C. to 100° C. or from 75° C. to 95° C. The temperature of the third residue in line 124 preferably is from 15° C. to 100° C., e.g., from 30° C. to 90° C. or from 50° C. to 80° C. Exemplary components of the distillate and residue compositions for third column 128 are provided in Table 5 below. It should be understood that the distillate and residue may also contain other components, not listed, such as components in the feed.

TABLE 5

THIRD COLUMN 128 (FIG. 1)

| | Conc. (wt. %) | Conc. (wt. %) | Conc. (wt. %) |
|---|---|---|---|
| Distillate | | | |
| Ethanol | 75 to 96 | 80 to 96 | 85 to 96 |
| Water | <12 | 1 to 9 | 3 to 8 |
| Acetic Acid | <12 | 0.0001 to 0.1 | 0.005 to 0.05 |
| Ethyl Acetate | <12 | 0.0001 to 0.05 | 0.005 to 0.025 |
| Acetaldehyde | <12 | 0.0001 to 0.1 | 0.005 to 0.05 |
| Acetal | <12 | 0.0001 to 0.05 | 0.005 to 0.01 |
| Residue | | | |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

In one embodiment, the third residue in line 124 is withdrawn from third column 128 at a temperature higher than the operating temperature of the second column 123.

Any of the compounds that are carried through the distillation process from the feed or crude reaction product generally remain in the third distillate in amounts of less 0.01 wt. %, based on the total weight of the third distillate composition, e.g., less than 0.05 wt. % or less than 0.02 wt. %. In one embodiment, one or more side streams may remove impurities from any of the columns in the system 100. Preferably at least one side stream is used to remove impurities from the third column 128. The impurities may be purged and/or retained within the system 100.

The third distillate in line 129 may be further purified to form an anhydrous ethanol product stream, i.e., "finished anhydrous ethanol," using one or more additional separation systems, such as, for example, distillation columns, adsorption units, membranes, or molecular sieves. Suitable adsorption units include pressure swing adsorption units and thermal swing adsorption unit.

Returning to second column 123, the second distillate preferably is refluxed as shown in FIG. 1, optionally at a reflux ratio of 1:10 to 10:1, e.g., from 1:5 to 5:1 or from 1:3 to 3:1. In one embodiment, at least a portion of second distillate in line 127 is further processed in fourth column 131, also referred to as the "acetaldehyde removal column." In fourth column 131, the second distillate is separated into a fourth distillate, which comprises acetaldehyde, in line 132 and a fourth residue, which comprises ethyl acetate, in line 133. The fourth distillate preferably is refluxed at a reflux ratio from 1:20 to 20:1, e.g., from 1:15 to 15:1 or from 1:10 to 10:1, and at least a portion of the fourth distillate is returned to vaporizer 108. Additionally, at least a portion of fourth distillate in line 132 may be purged. Without being bound by theory, since acetaldehyde may be reacted, e.g., by hydrogenation, to form ethanol, the recycling of a stream that contains acetaldehyde to the reaction zone increases the yield of ethanol and decreases byproduct and waste generation. In another embodiment, the acetaldehyde may be collected and utilized, with or without further purification, to make useful products including but not limited to n-butanol, 1,3-butanediol, and/or crotonaldehyde and derivatives.

The fourth residue of fourth column 131 may be purged via line 133. The fourth residue primarily comprises ethyl acetate and ethanol, which may be suitable for use as a solvent mixture or in the production of esters. In one preferred embodiment, the acetaldehyde is removed from the second distillate in fourth column 131 such that no detectable amount of acetaldehyde is present in the residue of column 131.

Fourth column 131 is a tray column as described above and may operate above atmospheric pressure. In one embodiment, the pressure is from 120 kPa to 5,000 kPa, e.g., from 200 kPa to 4,500 kPa, or from 400 kPa to 3,000 kPa. In a preferred embodiment the fourth column 131 may operate at a pressure that is higher than the pressure of the other columns.

The temperature of the fourth distillate exiting in line 132 preferably is from 60° C. to 110° C., e.g., from 70° C. to 100° C. or from 75° C. to 95° C. The temperature of the residue in line 133 preferably is from 70° C. to 115° C., e.g., from 80° C. to 110° C. or from 85° C. to 110° C. Exemplary components of the distillate and residue compositions for fourth column 131 are provided in Table 6 below. It should be understood that the distillate and residue may also contain other components, not listed, such as components in the feed.

TABLE 6

FOURTH COLUMN 131 (FIG. 1)

| | Conc. (wt. %) | Conc. (wt. %) | Conc. (wt. %) |
|---|---|---|---|
| Distillate | | | |
| Acetaldehyde | 2 to 80 | 2 to 50 | 5 to 40 |
| Ethyl Acetate | <90 | 30 to 80 | 40 to 75 |
| Ethanol | <30 | 0.001 to 25 | 0.01 to 20 |
| Water | <25 | 0.001 to 20 | 0.01 to 15 |
| Residue | | | |
| Ethyl Acetate | 40 to 100 | 50 to 100 | 60 to 100 |
| Ethanol | <40 | 0.001 to 30 | 0.01 to 15 |
| Water | <25 | 0.001 to 20 | 2 to 15 |
| Acetaldehyde | <1 | 0.001 to 0.5 | Not detectable |
| Acetal | <3 | 0.0001 to 2 | 0.001 to 0.01 |

In one embodiment, a portion of the third residue in line 124 is recycled to second column 123. In one embodiment, recycling the third residue further reduces the aldehyde components in the second residue and concentrates these aldehyde components in second distillate in line 127 and thereby sent to fourth column 131, wherein the aldehydes may be more easily separated. The third distillate in line 129 may have lower concentrations of aldehydes and esters due to the recycling of third residue in line 124.

Figure 2:
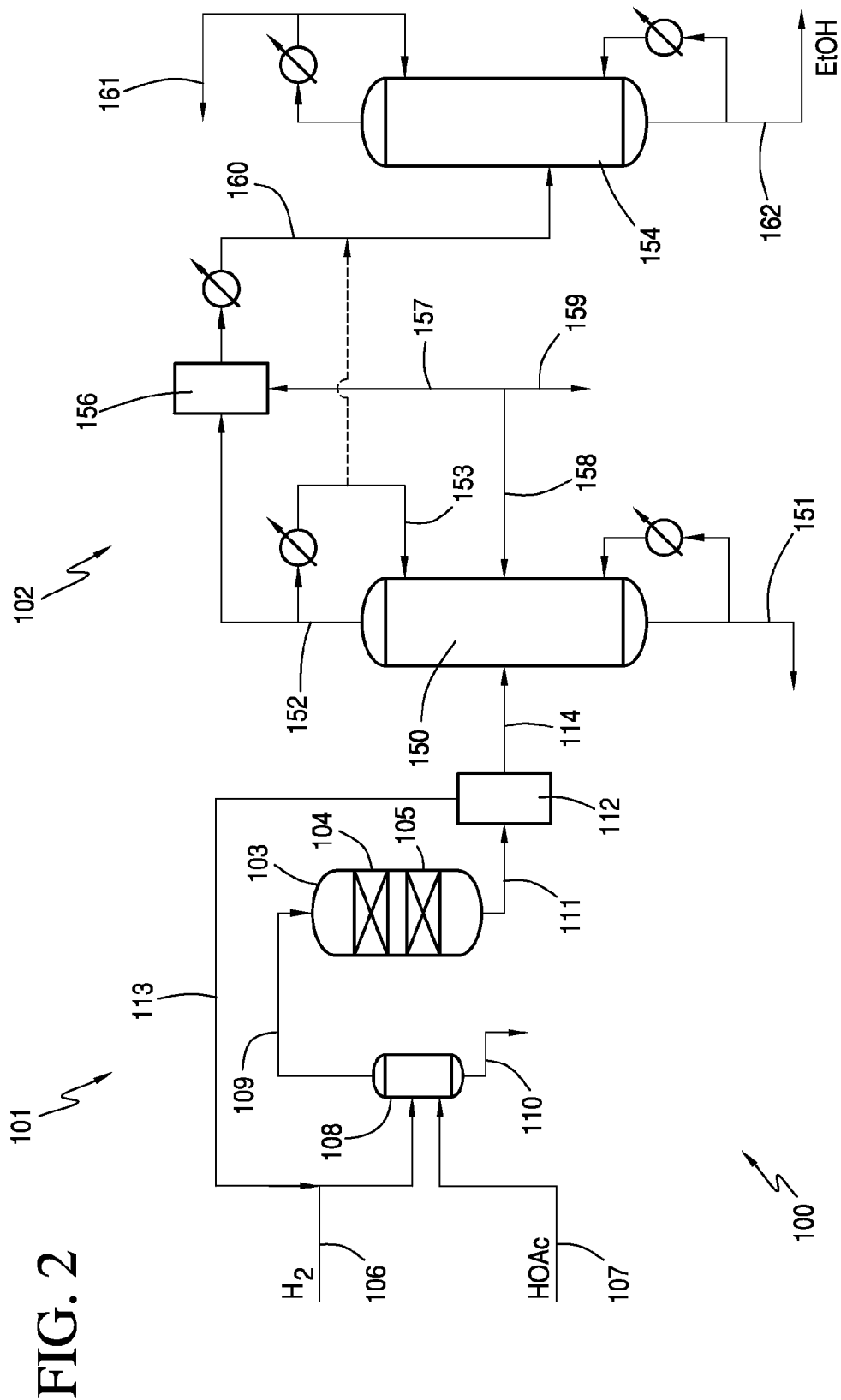
FIG. 2 is a schematic diagram of another hydrogenation process having a stacked bed reactor with two columns and an intervening water removal in accordance with an embodiment of the present invention.

FIG. 2 illustrates another exemplary separation system. The reaction zone 101 of FIG. 2 is similar to FIG. 1 and produces a liquid stream 114, e.g., crude ethanol product, for further separation. In one preferred embodiment, the reaction zone 101 of FIG. 2, in particular first bed 104, operates at above 80% acetic acid conversion, e.g., above 90% conversion or above 99% conversion. Thus, the acetic acid concentration in the liquid stream 114 may be low.

Liquid stream 114 is introduced in the middle or lower portion of a first column 150, also referred to as acid-water column. For purposes of convenience, the columns in each exemplary separation process, may be referred as the first, second, third, etc., columns, but it is understood that first column 150 in FIG. 2 operates differently than the first column 120 of FIG. 1. In one embodiment, no entrainers are added to first column 150. In FIG. 2, first column 150, water and unreacted acetic acid, along with any other heavy components, if present, are removed from liquid stream 114 and are withdrawn, preferably continuously, as a first residue in line 151. Preferably, a substantial portion of the water in the crude ethanol product that is fed to first column 150 may be removed in the first residue, for example, up to about 75% or to about 90% of the water from the crude ethanol product. First column 150 also forms a first distillate, which is withdrawn in line 152.

When column 150 is operated under about 170 kPa, the temperature of the residue exiting in line 151 preferably is from 90° C. to 130° C., e.g., from 95° C. to 120° C. or from 100° C. to 115° C. The temperature of the distillate exiting in line 152 preferably is from 60° C. to 90° C., e.g., from 65° C. to 85° C. or from 70° C. to 80° C. In some embodiments, the pressure of first column 150 may range from 0.1 kPa to 510 kPa, e.g., from 1 kPa to 475 kPa or from 1 kPa to 375 kPa.

The first distillate in line 152 comprises water, in addition to ethanol and other organics. In terms of ranges, the concentration of water in the first distillate in line 152 preferably is from 4 wt. % to 38 wt. %, e.g., from 7 wt. % to 32 wt. %, or from 7 to 25 wt. %. A portion of first distillate in line 153 may be condensed and refluxed, for example, at a ratio from 10:1 to 1:10, e.g., from 3:1 to 1:3 or from 1:2 to 2:1. It is understood that reflux ratios may vary with the number of stages, feed locations, column efficiency and/or feed composition. Operating with a reflux ratio of greater than 3:1 may be less preferred because more energy may be required to operate the first column 150. The condensed portion of the first distillate may also be fed to a second column 154.

The remaining portion of the first distillate in 152 is fed to a water separation unit 156. Water separation unit 156 may be an adsorption unit, membrane, molecular sieves, extractive column distillation, or a combination thereof. A membrane or an array of membranes may also be employed to separate water from the distillate. The membrane or array of membranes may be selected from any suitable membrane that is capable of removing a permeate water stream from a stream that also comprises ethanol and ethyl acetate.

In a preferred embodiment, water separator 156 is a pressure swing adsorption (PSA) unit. The PSA unit is optionally operated at a temperature from 30° C. to 160° C., e.g., from 80° C. to 140° C., and a pressure from 0.01 kPa to 550 kPa, e.g., from 1 kPa to 150 kPa. The PSA unit may comprise two to five beds. Water separator 156 may remove at least 95% of the water from the portion of first distillate in line 152, and more preferably from 99% to 99.99% of the water from the first distillate, in a water stream 157. All or a portion of water stream 157 may be returned to column 150 in line 158, where the water preferably is ultimately recovered from column 150 in the first residue in line 151. Additionally or alternatively, all or a portion of water stream 157 may be purged via line 159. The remaining portion of first distillate exits the water separator 156 as ethanol mixture stream 160. Ethanol mixture stream 160 may have a low concentration of water of less than 10 wt. %, e.g., less than 6 wt. % or less than 2 wt. %. Exemplary components of ethanol mixture stream 160 and first residue in line 151 are provided in Table 7 below. It should also be understood that these streams may also contain other components, not listed, such as components derived from the feed.

TABLE 7

FIRST COLUMN 150 WITH PSA (FIG. 2)

|  | Conc. (wt. %) | Conc. (wt. %) | Conc. (wt. %) |
|---|---|---|---|
| Ethanol Mixture Stream |  |  |  |
| Ethanol | 20 to 95 | 30 to 95 | 40 to 95 |
| Water | <10 | 0.01 to 6 | 0.1 to 2 |
| Acetic Acid | <2 | 0.001 to 0.5 | 0.01 to 0.2 |
| Ethyl Acetate | <60 | 1 to 55 | 5 to 55 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue |  |  |  |
| Acetic Acid | <90 | 1 to 50 | 2 to 35 |
| Water | 30 to 100 | 45 to 95 | 60 to 90 |
| Ethanol | <1 | <0.9 | <0.3 |

Preferably, ethanol mixture stream 160 is not returned or refluxed to first column 150. The condensed portion of the first distillate in line 153 may be combined with ethanol mixture stream 160 to control the water concentration fed to the second column 154. For example, in some embodiments the first distillate may be split into equal portions, while in other embodiments, all of the first distillate may be condensed or all of the first distillate may be processed in the water separation unit. In FIG. 2, the condensed portion in line 153 and ethanol mixture stream 160 are co-fed to second column 154. In other embodiments, the condensed portion in line 153 and ethanol mixture stream 160 may be separately fed to second column 154. The combined distillate and ethanol mixture has a total water concentration of greater than 0.5 wt. %, e.g., greater than 2 wt. % or greater than 5 wt. %. In terms of ranges, the total water concentration of the combined distillate and ethanol mixture may be from 0.5 to 15 wt. %, e.g., from 2 to 12 wt. %, or from 5 to 10 wt. %.

The second column 154 in FIG. 2, also referred to as the "light ends column," removes ethyl acetate and acetaldehyde from the first distillate in line 153 and/or ethanol mixture stream 160. Ethyl acetate and acetaldehyde are removed as a second distillate in line 161 and ethanol is removed as the second residue in line 162. Second column 108 may be a tray column or packed column. In one embodiment, second column 154 is a tray column having from 5 to 70 trays, e.g., from 15 to 50 trays or from 20 to 45 trays.

Second column 154 operates at a pressure ranging from 0.1 kPa to 510 kPa, e.g., from 10 kPa to 450 kPa or from 50 kPa to 350 kPa. Although the temperature of second column 154 may vary, when at about 20 kPa to 70 kPa, the temperature of the second residue exiting in line 162 preferably is from 30° C. to 75° C., e.g., from 35° C. to 70° C. or from 40° C. to 65° C. The temperature of the second distillate exiting in line 161 preferably is from 20° C. to 55° C., e.g., from 25° C. to 50° C. or from 30° C. to 45° C.

The total concentration of water fed to second column 154 preferably is less than 10 wt. %, as discussed above. When first distillate in line 153 and/or ethanol mixture stream comprises minor amounts of water, e.g., less than 1 wt. % or less than 0.5 wt. %, additional water may be fed to the second column 154 as an extractive agent in the upper portion of the column. A sufficient amount of water is preferably added via the extractive agent such that the total concentration of water fed to second column 154 is from 1 to 10 wt. % water, e.g., from 2 to 6 wt. %, based on the total weight of all components fed to second column 154. If the extractive agent comprises water, the water may be obtained from an external source or from an internal return/recycle line from one or more of the other columns or water separators.

Suitable extractive agents may also include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof. When extractive agents are used, a suitable recovery system, such as a further distillation column, may be used to recycle the extractive agent.

Exemplary components for the second distillate and second residue compositions for the second column 154 are provided in Table 8, below. It should be understood that the distillate and residue may also contain other components, not listed in Table 8.

TABLE 8

SECOND COLUMN 154 (FIG. 2)

|  | Conc. (wt. %) | Conc. (wt. %) | Conc. (wt. %) |
|---|---|---|---|
| Second Distillate |  |  |  |
| Ethyl Acetate | 5 to 90 | 10 to 80 | 15 to 75 |
| Acetaldehyde | <60 | 1 to 40 | 1 to 35 |

TABLE 8-continued

SECOND COLUMN 154 (FIG. 2)

|  | Conc. (wt. %) | Conc. (wt. %) | Conc. (wt. %) |
|---|---|---|---|
| Ethanol | <45 | 0.001 to 40 | 0.01 to 35 |
| Water | <20 | 0.01 to 10 | 0.1 to 5 |
| Second Residue | | | |
| Ethanol | 80 to 99.5 | 85 to 97 | 60 to 95 |
| Water | <20 | 0.001 to 15 | 0.01 to 10 |
| Ethyl Acetate | <1 | 0.001 to 2 | 0.001 to 0.5 |
| Acetic Acid | <0.5 | <0.01 | 0.001 to 0.01 |
| Acetal | <0.05 | <0.03 | <0.01 |

The second residue in FIG. 2 comprises one or more impurities selected from the group consisting of ethyl acetate, acetic acid, and acetaldehyde. The second residue may comprise at least 100 wppm of these impurities, e.g., at least 250 wppm or at least 500 wppm. In some embodiments, the second residue may contain substantially no ethyl acetate or acetaldehyde.

The second distillate in line 161, which comprises ethyl acetate and/or acetaldehyde, preferably is refluxed as shown in FIG. 2, for example, at a reflux ratio from 1:30 to 30:1, e.g., from 1:10 to 10:1 or from 1:3 to 3:1. Additionally, at least a portion of second distillate 161 may be purged.

Figure 3:
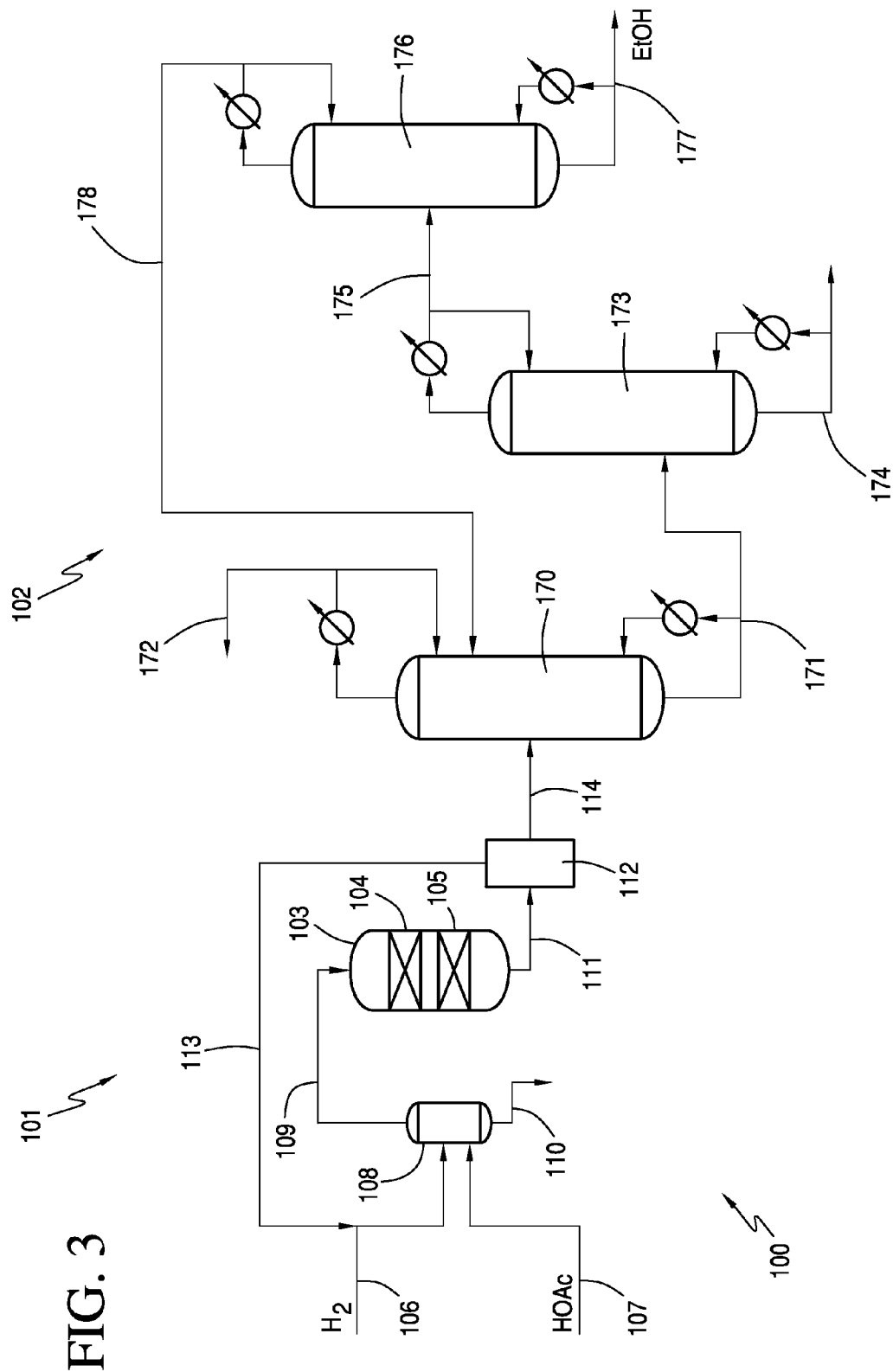
FIG. 3 is a schematic diagram of yet another hydrogenation process having a stacked bed reactor with three columns in accordance with an embodiment of the present invention.

FIG. 3 illustrates another exemplary separation system. The reaction zone 101 of FIG. 3 is similar to FIG. 1 and produces a liquid stream 114, e.g., crude ethanol product, for further separation. In one preferred embodiment, the reaction zone 101 of FIG. 3, in particular first bed 104, operates at above 80% acetic acid conversion, e.g., above 90% conversion or above 99% conversion. Thus, the acetic acid concentration in the liquid stream 114 may be low.

In the exemplary embodiment shown in FIG. 3, liquid stream 114 is introduced in the lower part of first column 170, e.g., lower half or middle third. In one embodiment, no entrainers are added to first column 170. In first column 170, a weight majority of the ethanol, water, acetic acid, and other heavy components, if present, are removed from liquid stream 114 and are withdrawn, preferably continuously, as residue in line 171. First column 170 also forms an overhead distillate, which is withdrawn in line 172, and which may be condensed and refluxed, for example, at a ratio from 30:1 to 1:30, e.g., from 10:1 to 1:10 or from 1:5 to 5:1. The overhead distillate in stream 172 preferably comprises a weight majority of the ethyl acetate from liquid stream 114.

When column 170 is operated under about 170 kPa, the temperature of the residue exiting in line 171 preferably is from 70° C. to 155° C., e.g., from 90° C. to 130° C. or from 100° C. to 110° C. The base of column 170 may be maintained at a relatively low temperature by withdrawing a residue stream comprising ethanol, water, and acetic acid, thereby providing an energy efficiency advantage. The temperature of the distillate exiting in line 172 from column 170 preferably at 170 kPa is from 75° C. to 100° C., e.g., from 75° C. to 83° C. or from 81° C. to 84° C. In some embodiments, the pressure of first column 170 may range from 0.1 kPa to 510 kPa, e.g., from 1 kPa to 475 kPa or from 1 kPa to 375 kPa. Exemplary components of the distillate and residue compositions for first column 170 are provided in Table 9 below. It should also be understood that the distillate and residue may also contain other components, not listed in Table 9.

TABLE 9

FIRST COLUMN 170 (FIG. 3)

|  | Conc. (wt. %) | Conc. (wt. %) | Conc. (wt. %) |
|---|---|---|---|
| Distillate | | | |
| Ethyl Acetate | 10 to 85 | 15 to 80 | 20 to 75 |
| Acetaldehyde | 0.1 to 70 | 0.2 to 65 | 0.5 to 65 |
| Diethyl Acetal | 0.01 to 10 | 0.01 to 6 | 0.01 to 5 |
| Acetone | <0.05 | 0.001 to 0.03 | 0.01 to 0.025 |
| Ethanol | 3 to 55 | 4 to 50 | 5 to 45 |
| Water | 0.1 to 20 | 1 to 15 | 2 to 10 |
| Acetic Acid | <2 | <0.1 | <0.05 |
| Residue | | | |
| Acetic Acid | 0.01 to 35 | 0.1 to 30 | 0.2 to 25 |
| Water | 5 to 40 | 10 to 35 | 15 to 30 |
| Ethanol | 10 to 75 | 15 to 70 | 20 to 65 |

In an embodiment of the present invention, column 170 may be operated at a temperature where most of the water, ethanol, and acetic acid are removed from the residue stream and only a small amount of ethanol and water is collected in the distillate stream due to the formation of binary and tertiary azeotropes. The weight ratio of water in the residue in line 171 to water in the distillate in line 172 may be greater than 1:1, e.g., greater than 2:1. The weight ratio of ethanol in the residue to ethanol in the distillate may be greater than 1:1, e.g., greater than 2:1

The amount of acetic acid in the first residue may vary depending primarily on the conversion in stacked bed reactor 103. In one embodiment, when the conversion is high, e.g., greater than 90%, the amount of acetic acid in the first residue may be less than 10 wt. %, e.g., less than 5 wt. % or less than 2 wt. %. In other embodiments, when the conversion is lower, e.g., less than 90%, the amount of acetic acid in the first residue may be greater than 10 wt. %.

The distillate preferably is substantially free of acetic acid, e.g., comprising less than 1000 wppm, less than 500 wppm or less than 100 wppm acetic acid. The distillate may be purged from the system or recycled in whole or part to reactor 103. In some embodiments, the distillate may be further separated, e.g., in a distillation column (not shown), into an acetaldehyde stream and an ethyl acetate stream. Either of these streams may be returned to the reactor 103 or separated from system 100 as a separate product.

Some species, such as acetals, may decompose in first column 170 such that very low amounts, or even no detectable amounts, of acetals remain in the distillate or residue.

To recover ethanol, the residue in line 171 may be further separated in a second column 173, also referred to as an "acid separation column." An acid separation column may be used when the acetic acid concentration in the first residue is greater than 1 wt. %, e.g., greater than 5 wt. %. The first residue in line 171 is introduced to second column 173 preferably in the top part of column 173, e.g., top half or top third. Second column 173 yields a second residue in line 174 comprising acetic acid and water, and a second distillate in line 175 comprising ethanol. Second column 173 may be a tray column or packed column. In one embodiment, second column 173 is a tray column having from 5 to 150 trays, e.g., from 15 to 50 trays or from 20 to 45 trays. Although the temperature and pressure of second column 173 may vary, when at atmospheric pressure the temperature of the second residue exiting in line 174 preferably is from 95° C. to 130° C., e.g., from 100° C. to 125° C. or from 110° C. to 120° C. The temperature of the second distillate exiting in line 175 preferably is from 60° C. to 100° C., e.g., from 75° C. to 100°

C. or from 80° C. to 100° C. The pressure of second column 173 may range from 0.1 kPa to 510 kPa, e.g., from 1 kPa to 475 kPa or from 1 kPa to 375 kPa. Exemplary components for the distillate and residue compositions for second column 173 are provided in Table 10 below. It should be understood that the distillate and residue may also contain other components, not listed in Table 10.

TABLE 10

SECOND COLUMN 173 (FIG. 3)

|  | Conc. (wt. %) | Conc. (wt. %) | Conc. (wt. %) |
|---|---|---|---|
| Second Distillate |  |  |  |
| Ethanol | 70 to 99.9 | 75 to 98 | 80 to 95 |
| Ethyl Acetate | <10 | 0.001 to 5 | 0.01 to 3 |
| Acetaldehyde | <5 | 0.001 to 1 | 0.005 to 0.5 |
| Acetal | 0.01 to 10 | 0.01 to 6 | 0.01 to 5 |
| Water | 0.1 to 30 | 1 to 25 | 5 to 20 |
| Second Residue |  |  |  |
| Acetic Acid | 0.1 to 45 | 0.2 to 40 | 0.5 to 35 |
| Water | 45 to 100 | 55 to 99.8 | 65 to 99.5 |
| Ethyl Acetate | <2 | <1 | <0.5 |
| Ethanol | <5 | 0.001 to 5 | <2 |

The weight ratio of ethanol in the second distillate in line 175 to ethanol in the second residue in line 174 preferably is at least 35:1. In one embodiment, the weight ratio of water in the second residue 174 to water in the second distillate 175 is greater than 2:1, e.g., greater than 4:1 or greater than 6:1. In addition, the weight ratio of acetic acid in the second residue 174 to acetic acid in the second distillate 175 preferably is greater than 10:1, e.g., greater than 15:1 or greater than 20:1. Preferably, the second distillate in line 175 is substantially free of acetic acid and may only contain, if any, trace amounts of acetic acid.

As shown, the second distillate in line 175 is fed to a third column 176, e.g., ethanol product column, for separating the second distillate into a third distillate (ethyl acetate distillate) in line 178 and a third residue (ethanol residue) in line 177. Second distillate in line 175 may be introduced into the lower part of column 176, e.g., lower half or lower third. Third distillate 178 is preferably refluxed, for example, at a reflux ratio greater than 2:1, e.g., greater than 5:1 or greater than 10:1. Additionally, at least a portion of third distillate 178 may be purged. Third column 176 is preferably a tray column as described herein and preferably operates at atmospheric pressure. The temperature of the third residue exiting from third column 176 preferably is from 60° C. to 110° C., e.g., from 70° C. to 100° C. or from 75° C. to 95° C. The temperature of the third distillate exiting from third column 176 preferably is from 70° C. to 115° C., e.g., from 80° C. to 110° C. or from 85° C. to 105° C., when the column is operated at atmospheric pressure.

In one embodiment, third distillate in line 178 may be introduced into first column 170.

The remaining water from the second distillate in line 175 may be removed in further embodiments of the present invention. Depending on the water concentration, the ethanol product may be derived from the second distillate in line 175 or the third residue in line 177 Some applications, such as industrial ethanol applications, may tolerate water in the ethanol product, while other applications, such as fuel applications, may require an anhydrous ethanol. The amount of water in the distillate of line 175 or the residue of line 177 may be closer to the azeotropic amount of water, e.g., at least 4 wt. %, preferably less than 20 wt. %, e.g., less than 12 wt. % or less than 7.5 wt. %. Water may be removed from the second distillate in line 175 or the third residue in line 177 using several different separation techniques as described herein. Particularly preferred techniques include the use of distillation column, membranes, adsorption units, and combinations thereof.

Some of the residues withdrawn from the separation zone 102 comprise acetic acid and water. Depending on the amount of water and acetic acid contained in the residue of first column, e.g., 120 in FIG. 1, 150 in FIG. 2, or residue of second column 173 in FIG. 3, the residue may be treated in one or more of the following processes. The following are exemplary processes for further treating the residue and it should be understood that any of the following may be used regardless of acetic acid concentration. When the residue comprises a majority of acetic acid, e.g., greater than 70 wt. %, the residue may be recycled to the reactor without any separation of the water. In one embodiment, the residue may be separated into an acetic acid stream and a water stream when the residue comprises a majority of acetic acid, e.g., greater than 50 wt. %. Acetic acid may also be recovered in some embodiments from the residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to the reactor 108. The resulting water stream may be used as an extractive agent or to hydrolyze an ester-containing stream in a hydrolysis unit.

In other embodiments, for example, where the residue comprises less than 50 wt. % acetic acid, possible options include one or more of: (i) returning a portion of the residue to reactor 108, (ii) neutralizing the acetic acid, (iii) reacting the acetic acid with an alcohol, or (iv) disposing of the residue in a waste water treatment facility. It also may be possible to separate a residue comprising less than 50 wt. % acetic acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the residue comprises very minor amounts of acetic acid, e.g., less than 5 wt. % or less than 1 wt. %, the residue may be neutralized and/or diluted before being disposed of to a waste water treatment facility. The organic content, e.g., acetic acid content, of the residue beneficially may be suitable to feed microorganisms used in a waste water treatment facility.

Figure 4:
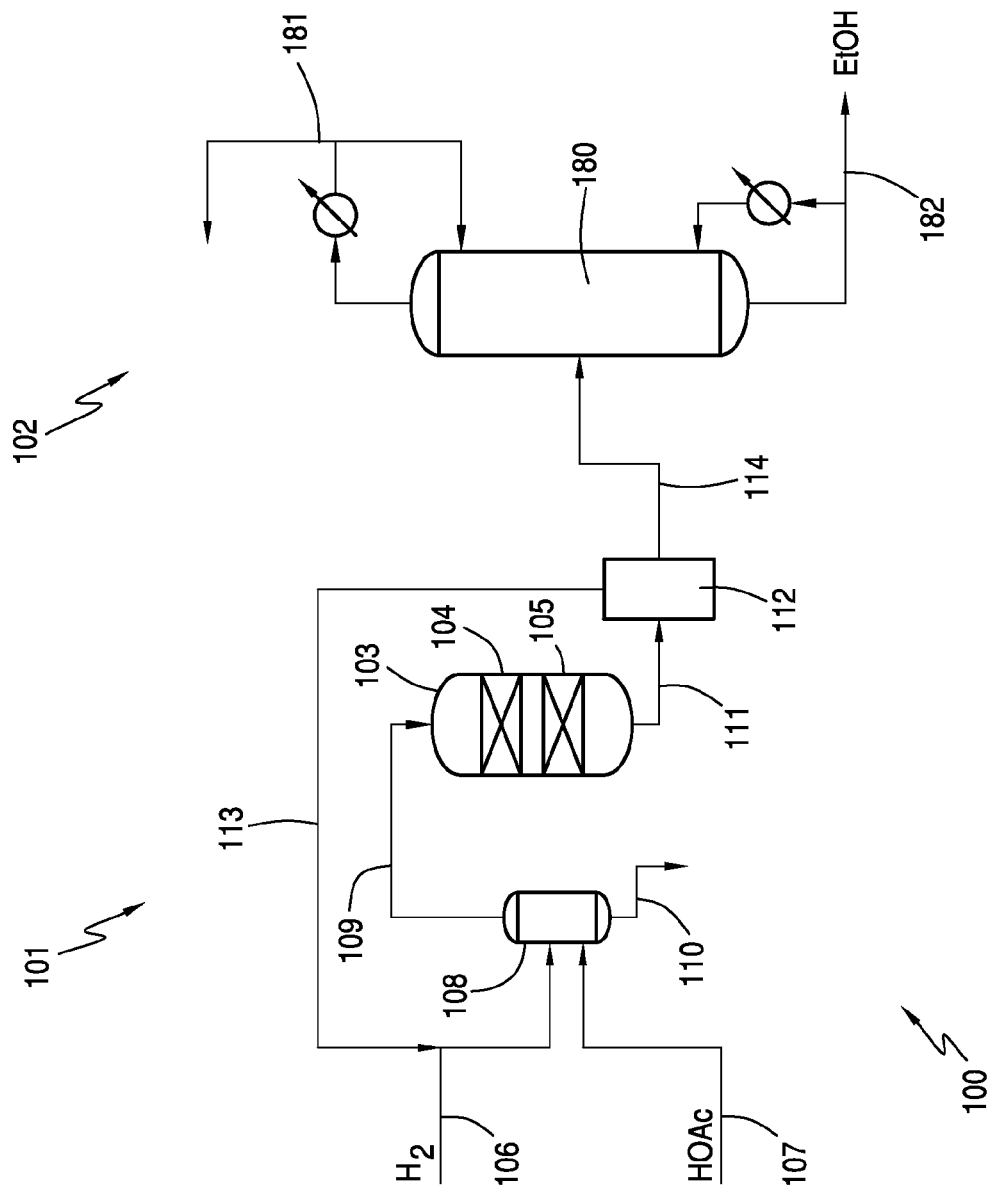
FIG. 4 is a schematic diagram of yet another hydrogenation process having a stacked bed reactor with a single column in accordance with an embodiment of the present invention.
Figure 5:
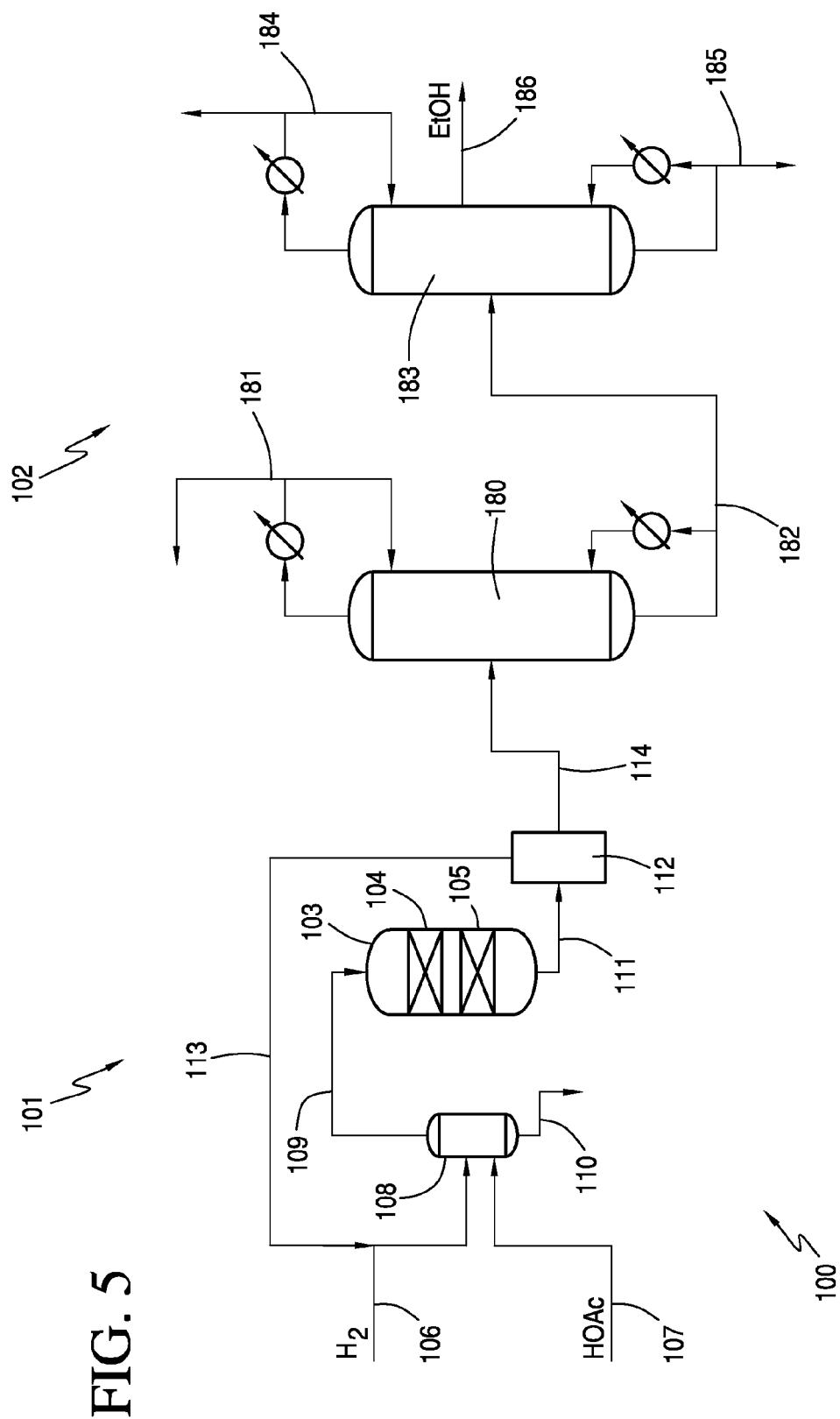
FIG. 5 is a schematic diagram of yet another hydrogenation process having a stacked bed reactor with a heavy ends column in accordance with an embodiment of the present invention.

In some embodiments, liquid stream 114 may contain substantially no acetic acid. In FIGS. 4 and 5, liquid stream 114 may be fed to a first column 180 for separating ethanol and ethyl acetate. In FIG. 5, there is an additional heavy column to remove any heavies from the ethanol product.

Liquid stream 114 is introduced to the side of a first distillation column 180, also referred to as a "light ends column," to yield a first distillate in line 181 comprising ethyl acetate and a first residue in line 182 comprising ethanol. Preferably the distillation column operates to maintain a low concentration of ethyl acetate in the residue, e.g., less than 1 wt. %, less than 0.1 wt. % or less than 0.01 wt. %. The distillate of column 180 preferably is refluxed at a ratio sufficient to maintain low concentrations of ethyl acetate in the residue and minimize ethanol concentrations in the distillate, and reflux ratio may vary from 30:1 to 1:30, e.g., from 10:1 to 1:10 or from 5:1 to 1:5.

Distillation column 180 may be a tray column or packed column. In one embodiment, distillation column 180 is a tray column having from 5 to 110 trays, e.g., from 15 to 90 trays or from 20 to 80 trays. Distillation column 180 operates at a pressure ranging from 20 kPa to 500 kPa, e.g., from 50 kPa to 300 kPa or from 80 kPa to 200 kPa. Without being bound by theory, lower pressures of less than 100 kPa or less than 70 kPa, may further enhance separation of liquid stream 114. Although the temperature of distillation column 180 may vary, when at atmospheric pressure, the temperature of the distillate exiting in line 181 preferably is from 40° C. to 90° C., e.g., from 45° C. to 85° C. or from 50° C. to 80° C. The temperature of the residue exiting in line 182 preferably is from 45° C. to 95° C., e.g., from 50° C. to 90° C. or from 60° C. to 85° C.

Exemplary compositions of the first column 180 are shown in Table 11 below. It should be understood that the distillate and residue may also contain other components, not listed in Table 11.

TABLE 11

FIRST COLUMN 180 (FIG. 4)

|  | Conc. (wt. %) | Conc. (wt. %) | Conc. (wt. %) |
|---|---|---|---|
| Distillate |  |  |  |
| Ethyl Acetate | 20 to 80 | 25 to 75 | 30 to 70 |
| Ethanol | 0.01 to 45 | 1 to 35 | 2 to 30 |
| Water | <10 | <5 | <3 |
| Acetaldehyde | 0.01 to 30 | 0.1 to 20 | 1 to 10 |
| Isopropanol | 0.001 to 0.5 | 0.001 to 0.1 | 0.001 to 0.05 |
| Acetone | 0.001 to 3 | 0.001 to 1 | 0.001 to 0.5 |
| Diethyl acetal | 0.001 to 3 | 0.001 to 1 | 0.01 to 0.5 |
| Carbon Gases | 0.001 to 2 | 0.001 to 1 | 0.001 to 0.5 |
| Residue |  |  |  |
| Ethanol | 80 to 99.5 | 85 to 99.5 | 90 to 99.5 |
| Water | <20 | 0.001 to 15 | 0.01 to 10 |
| Ethyl Acetate | <0.01 | <0.001 | <0.0001 |
| Isopropanol | 0.001 to 3 | 0.001 to 1 | 0.001 to 0.5 |
| Acetone | 0.001 to 3 | 0.001 to 1 | 0.001 to 0.5 |
| Diethyl acetal | 0.001 to 3 | 0.001 to 1 | 0.01 to 0.5 |
| 2-butanol | 0.001 to 3 | 0.01 to 1 | 0.01 to 0.5 |
| n-butanol | <1 | <0.5 | <0.1 |
| Heavies | <1 | <0.5 | <0.1 |

Without being bound by theory, the presence of acetaldehyde in the crude reaction mixture from the hydrogenolysis reactor may produce several different impurities. The heavy impurities, such as higher alcohols, may build up in the first residue. In particular, 2-butanol has been found to be an impurity in this process. The weight ratio of 2-butanol to n-butanol in the first residue may be greater than 2:1, e.g., greater than 3:1 or greater than 5:1. Depending on the intended use of ethanol, these impurities may be of less significance. However, when a purer ethanol product is desired, a portion of first residue may be further separated in a finishing column 183 as shown in FIG. 5.

In some embodiments, it may be necessary to further treat the first residue to remove additional heavy compounds such as higher alcohols and any light components from the ethanol. As shown in FIG. 5, there is provided a finishing column 183, also referred to as a "second column." First residue in line 182 is fed to a lower portion of second column 183. Second column 183 produces an ethanol sidestream in line 186, a second distillate in line 184 and a second residue in line 185. Preferably ethanol sidestream in line 186 is the largest stream withdrawn from fourth column 183 and is withdrawn at a point above the feed point of the first residue in line 182. In one embodiment the relative flow ratios of sidestream to residue is greater than 50:1, e.g., greater than 100:1 or greater than 150:1.

Ethanol sidestream 186 preferably comprises at least 90% ethanol, e.g., at least 92% ethanol and a least 95% ethanol. Water concentration in ethanol sidestream 186 may be less than 10 wt. %, e.g., less than 5 wt. % or less than 1 wt. %. In addition, the amount of other impurities, in particular diethyl acetal and 2-butanol, are preferably less than 0.05 wt. %, e.g., less than 0.03 wt. % or less than 0.01 wt. %. The second distillate in line 184 preferably comprises a weight majority of the diethyl acetal fed to second column 183. In addition, other light components, such as acetaldehyde and/or ethyl acetate may also concentrate in the second distillate. The second residue in line 185 preferably comprises a weight majority of the 2-butanol fed to second column 183. Heavier alcohols may also concentrate in the fourth residue in line 185.

Second column 183 may be a tray column or packed column. In one embodiment, Second column 183 is a tray column having from 10 to 100 trays, e.g., from 20 to 80 trays or from 30 to 70 trays. Second column 183 operates at a pressure ranging from 1 kPa to 510 kPa, e.g., from 10 kPa to 450 kPa or from 50 kPa to 350 kPa. Although the temperature of second column 183 may vary, the temperature of the residue exiting in line 185 preferably is from 70° C. to 105° C., e.g., from 70° C. to 100° C. or from 75° C. to 95° C. The temperature of the second distillate exiting in line 184 preferably is from 50° C. to 90° C., e.g., from 55° C. to 85° C. or from 65° C. to 80° C. Ethanol sidestream 186 is preferably withdrawn at the boiling point of ethanol, about 78° C. at atmospheric pressure.

In some embodiments, a portion of the second residue, sidestream or second distillate may be dehydrated to form aliphatic alkenes. In one embodiment, the 2-butanol in the second residue may be dehydrated to 2-butene. In another embodiment, the 2-butanol in the second residue stream may be recovered in a separate system.

In one embodiment, instead of purging the second distillate in line 184 or the second residue in line 185, a portion thereof may be fed to vaporizer 108. Heavy ends compounds may be removed in the blowdown stream 110.

The ethanol product, either obtained as the second residue in line 182 of FIG. 4 or the sidestream in line 186 FIG. 5, may contain small concentrations of water. For some ethanol applications, in particular for fuel applications, it may be desirable to further reduce the water concentration. A portion of either ethanol stream may be fed to a water separation unit. Water separation unit may include an adsorption unit, one or more membranes, molecular sieves, extractive distillation units, or a combination thereof. Ethanol sidestream may be withdrawn as a vapor or liquid stream, but it may be more suitable to use a vapor stream. Suitable adsorption units include pressure swing adsorption (PSA) units and thermal swing adsorption (TSA) units. A PSA unit may be employed to remove water from the ethanol sidestream. PSA unit is operated at a temperature from 30° C. to 160° C., e.g., from 80° C. to 140° C., and a pressure from 0.01 kPa to 550 kPa, e.g., from 1 kPa to 150 kPa. The PSA unit may comprise two to five beds. The resulting dried ethanol product stream preferably has a water concentration that is less than 1 wt. %, e.g., less than 0.5 wt. % or less than 0.1 wt. %.

In some embodiments the desired ethanol product is an anhydrous ethanol that is suitable for uses as a fuel or as a blend for other fuels, such as gasoline. Water separation unit as described herein may be suitable for producing anhydrous ethanol.

The columns shown in FIGS. 1 to 5 may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in one or more columns, preferably two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

The ethanol product produced by the process of the present invention may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 12.

TABLE 12

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be higher than indicated in Table 12, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entireties of which is incorporated herein by reference. A zeolite catalyst, for example, may be employed as the dehydration catalyst. Preferably, the zeolite has a pore diameter of at least 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

In order that the invention disclosed herein may be more efficiently understood, examples are provided below. It should be understood that this example is for illustrative purposes only and is not to be construed as limiting the invention in any manner.

EXAMPLES

Example 1

A stacked bed reactor was loaded with 100 µl of a catalyst comprising 2 wt. % of 25 mol. % platinum and 75 mol. % tin on a high silica zeolite (HSZ™—Tosoh Products) support in a first bed. The stacked bed reactor also contained a second bed comprising 50 µl of a catalyst comprising 65 wt. % copper and 25 wt. % zinc on alumina. A reactant stream comprising 70 wt. % acetic acid and 30 wt. % ethyl acetate was fed to the reactor, along with hydrogen, at a GHSV of 1620 hr$^{-1}$.

Example 2

A stacked bed reactor was loaded with 100 µl of a catalyst comprising 2 wt. % of 25 mol. % platinum and 75 mol. % tin on a silica-alumina support in a first bed. The stacked bed reactor also contained a second bed comprising 50 µl of a catalyst comprising 65 wt. % copper and 25 wt. % zinc on alumina. A reactant stream comprising 70 wt. % acetic acid and 30 wt. % ethyl acetate was fed to the reactor, along with hydrogen, at a GHSV of 1620 hr$^{-1}$.

A feed comprising 70 wt. % acetic acid and 30 wt. % ethyl acetate was fed to reactors of Examples 1 and 2. The acetic acid and ethyl acetate conversions and ethanol and ethyl acetate selectivities are shown in Table 13. The values were measured at 20 hours time on stream and 60 hours.

TABLE 13

|  | Example 1 | | Example 2 | |
| --- | --- | --- | --- | --- |
| TOS (Hours) | 20 | 60 | 20 | 60 |
| Acetic Acid Conversion (%) | 90 | 70 | 83 | 99 |
| Ethanol Selectivity (%) | 45 | 38 | 40 | 59 |
| Ethyl Acetate Selectivity (%) | 57 | 63 | 50 | 42 |

Example 3

A stacked bed reactor was loaded with 100 µl of a catalyst comprising 1 wt. % platinum and 1.2 wt. % tin silica support modified with 6 wt. % calcium metasilicate in a first bed. The stacked bed reactor also contained a second bed comprising 50 µl of a catalyst comprising 65 wt. % copper and 25 wt. % zinc on alumina. A reactant stream comprising 70 wt. % acetic acid and 30 wt. % ethyl acetate was fed to the reactor, along with hydrogen, at a GHSV of 1620 hr$^{-1}$.

Example 4

A stacked bed reactor was loaded with 100 µl of a catalyst comprising 1 wt. % platinum and palladium, 0.1 wt. % cesium, 1.2 wt. % tin on a silica support modified with 14 wt. % of WO$_3$ in a first bed. The stacked bed reactor also contained a second bed comprising 50 µl of a catalyst comprising 65 wt. % copper and 25 wt. % zinc on alumina. A reactant stream comprising 70 wt. % acetic acid and 30 wt. % ethyl acetate was fed to the reactor, along with hydrogen, at a GHSV of 1620 hr$^{-1}$.

A feed comprising 70 wt. % acetic acid and 30 wt. % ethyl acetate was fed to reactors of Examples 3 and 4. The acetic acid and ethyl acetate conversions and ethanol and ethyl acetate selectivities are shown in Table 14. The values were measured at 20 hours time on stream and 60 hours.

TABLE 14

|  | Example 3 | | Example 4 | |
| --- | --- | --- | --- | --- |
| TOS (Hours) | 20 | 60 | 20 | 60 |
| Acetic Acid Conversion (%) | 90 | 83 | 99 | 99 |
| Ethanol Selectivity (%) | 78 | 82 | 75 | 78 |
| Ethyl Acetate Selectivity (%) | 22 | 18 | 22 | 22 |

Example 5

A stacked bed reactor was loaded with 230 µl of a catalyst comprising 2 wt. % of 25 mol. % platinum and 75 mol. % tin on a high silica zeolite (HSZ™—Tosoh Products) support in a first bed. The stacked bed reactor also contained a second bed comprising 100 µl of a catalyst comprising 65 wt. % copper and 25 wt. % zinc on alumina. A reactant stream comprising essentially pure acetic acid, e.g. greater than 99 wt. % acetic acid, was fed to the reactor, along with hydrogen, at a GHSV of 736 hr$^{-1}$.

Comparative Example A

This examples is similar to Example 5, except only the first catalyst from the first bed is used. There is no second catalyst.

Example 6

A stacked bed reactor was loaded with 230 µl of a catalyst comprising 2 wt. % of 25 mol. % platinum and 75 mol. % tin on a silica-alumina support in a first bed. The stacked bed reactor also contained a second bed comprising 100 µl of a catalyst comprising 65 wt. % copper and 25 wt. % zinc on alumina. A reactant stream comprising essentially pure acetic acid, e.g. greater than 99 wt. % acetic acid, was fed to the reactor, along with hydrogen, at a GHSV of 736 hr$^{-1}$.

Comparative Example B

Similar to Example 6, except only the first catalyst from the first bed is used. There is no second catalyst.

A feed comprising essentially pure acetic acid, e.g. greater than 99 wt. % acetic acid, was fed to reactors of Examples 5 and 6, and Comparative Examples A and B. The acetic acid and ethyl acetate conversions and ethanol and ethyl acetate selectivities are shown in Table 15. The values were measured at 20 hours time on stream and 60 hours.

TABLE 15

|  | Example 5 | | Comp. A | | Example 6 | | Comp. B | |
| --- | --- | --- | --- | --- | --- | --- | --- | --- |
| TOS (Hours) | 20 | 60 | 20 | 60 | 30 | 60 | 20 | 60 |
| Acetic Acid Conversion (%) | 99 | 99 | 60 | 80 | 99 | 99 | 78 | 83 |
| Ethanol Selectivity (%) | 85 | 81 | 18 | 25 | 95 | 95 | 20 | 30 |

TABLE 15-continued

| | Example 5 | | Comp. A | | Example 6 | | Comp. B | |
|---|---|---|---|---|---|---|---|---|
| TOS (Hours) | 20 | 60 | 20 | 60 | 30 | 60 | 20 | 60 |
| Ethyl Acetate Selectivity (%) | 5 | 5 | 80 | 75 | 5 | 5 | 76 | 70 |
| Methyl Acetate Selectivity (%) | 8.5 | 10.5 | 1 | 2 | 0.5 | 1 | 1 | 1 |

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol, comprising the steps of:
introducing a feed stream comprising from 5 to 40 wt. % ethyl acetate and from 60 to 95 wt. % acetic acid, and hydrogen into a stacked bed reactor that comprises a first bed and a second bed to produce a crude ethanol product, wherein the first bed comprises a first catalyst comprising platinum and tin on a first support and the second bed comprises a second catalyst comprising copper or an oxide thereof on a second support; and
recovering ethanol from the crude ethanol product in one or more columns.

2. The process of claim 1, wherein the feed stream comprises from 10 to 30 wt. % ethyl acetate and from 70 to 90 wt. % acetic acid.

3. The process of claim 1, wherein ethyl acetate conversion in the stacked bed reactor is greater than 0%.

4. The process of claim 1, wherein acetic acid conversion in the stacked bed reactor is greater than 60%.

5. The process of claim 1, wherein ethanol selectivity in the stacked bed reactor is greater than selectivity to ethyl acetate.

6. The process of claim 1, wherein ethanol selectivity is greater than 80%.

7. The process of claim 1, wherein methyl acetate selectivity is less than 5%.

8. The process of claim 1, wherein the ethyl acetate concentration of the feed is greater than the concentration of ethyl acetate in the crude ethanol product.

9. The process of claim 1, wherein the first support is selected from the group consisting of silica, silica/alumina, calcium metasilicate, pyrogenic silica, high purity silica, carbon, activated carbon, alumina, titania, zirconia, graphite, zeolites, and mixtures thereof.

10. The process of claim 9, wherein the first support further comprises one or more support modifiers.

11. The process of claim 10, wherein the support modifier is selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof.

12. The process of claim 10, wherein the support modifier is selected from the group consisting of $TiO_2$, $ZrO_2$, $Nb_2O_5$, $Ta_2O_5$, $Al_2O_3$, $B_2O_3$, $P_2O_5$, $Sb_2O_3$, $WO_3$, $MoO_3$, $Fe_2O_3$, $Cr_2O_3$, $V_2O_5$, $MnO_2$, $CuO$, $Co_2O_3$, and $Bi_2O_3$.

13. The process of claim 1, wherein the second catalyst further comprises zinc, aluminum, cobalt, or oxides thereof.

14. The process of claim 1, wherein the second support is selected from the group consisting of silica/alumina, alumina, titiana, zeolites, and mixtures thereof.

15. The process of claim 1, wherein the first support and second support each comprise alumina.

16. The process of claim 1, wherein the first catalyst further comprises one or more additional metals selected from the group consisting of palladium, cesium, and cobalt.

17. The process of claim 1, wherein the second catalyst further comprises one or more additional second metals selected from the group consisting of cobalt, rhodium, or iridium.

18. The process of claim 1, wherein the reaction in the stacked bed reactor is performed in a vapor phase at a temperature from 125° C. to 350° C., a pressure of 10 kPa to 3000 kPa, and a hydrogen to acetic acid mole ratio of greater than 4:1.

19. The process of claim 1, wherein the first bed has a volume that is larger than the second bed.

20. The process of claim 1, further comprising gasifying a carbonaceous material to produce the feed stream, wherein the carbonaceous material is selected from the group consisting of oil, coal, natural gas and biomass.

21. A process for producing ethanol, comprising the steps of:
introducing hydrogen and a feed stream comprising from 5 to 40 wt. % ethyl acetate and 60 to 95 wt. % acetic acid into a stacked bed reactor that comprises a first bed and a second bed to produce a crude ethanol product, wherein the first bed comprises a first catalyst comprising platinum and tin on a first support comprising a support modifier selected from the group consisting of $WO_3$, $MoO_3$, $Fe_2O_3$, $Cr_2O_3$, $Nb_2O_5$, $V_2O_5$, $MnO_2$, $CuO$, $Co_2O_3$, and $Bi_2O_3$, and the second bed comprises a second catalyst comprising copper or an oxide thereof on a second support; and
recovering ethanol from the crude ethanol product in one or more columns.

22. The process of claim 21, wherein the feed stream comprises 30 wt. % ethyl acetate and 70 wt. % acetic acid.

23. The process of claim 21, wherein ethyl acetate conversion in the stacked bed reactor is greater than 0% and acetic acid conversion in the stacked bed reactor is greater than 60%.

24. The process of claim 21, wherein ethanol selectivity in the stacked bed reactor is greater than the selectivity to ethyl acetate.

25. The process of claim 21, wherein ethanol selectivity is greater than 80%.

26. A process for producing ethanol, comprising the steps of:
introducing hydrogen and a feed stream comprising from 5 to 40 wt. % ethyl acetate and from 60 to 95 wt. % acetic acid into a stacked bed reactor that comprises a first bed and a second bed to produce a crude ethanol product, wherein the first bed comprises a first catalyst comprising platinum and tin on a first support, and the second bed comprises a second catalyst comprising copper or an oxide thereof on a second support, and wherein the first support and second support each comprise alumina; and
recovering ethanol from the crude ethanol product in one or more columns.

27. The process of claim 26, wherein the feed stream comprises from 10 to 30 wt. % ethyl acetate and from 70 to 90 wt. % acetic acid.

28. The process of claim 26, wherein ethyl acetate conversion in the stacked bed reactor is greater than 0%.

29. The process of claim 26, wherein acetic acid conversion in the stacked bed reactor is greater than 60%, and wherein ethanol selectivity in the stacked bed reactor is greater than selectivity to ethyl acetate.

30. The process of claim 26, wherein ethanol selectivity is greater than 80%.

31. A process for producing ethanol, comprising the steps of:
introducing hydrogen and a feed stream comprising from 5 to 40 wt. % ethyl acetate and from 60 to 95 wt. % acetic acid into a stacked bed reactor that comprises a first bed and a second bed to produce a crude ethanol product, wherein the first bed has a bed volume that is larger than the second bed, wherein the first bed comprises a first catalyst, and the second bed comprises a second catalyst that is different than the first catalyst; and
recovering ethanol from the crude ethanol product in one or more columns.

32. The process of claim 31, wherein acetic acid conversion in the first bed is greater than 97%.

33. The process of claim 31, wherein the bed volume of the first bed is at least twice as large as the second bed.

34. The process of claim 31, wherein acetic acid concentration fed to the second bed is less than 3 wt. %.

* * * * *